US007709533B2

(12) United States Patent
Wang et al.

(10) Patent No.: US 7,709,533 B2
(45) Date of Patent: May 4, 2010

(54) IMINES AS ION CHANNEL MODULATORS

(75) Inventors: Xiaodong Wang, Chapel Hill, NC (US); Alan Bradley Fulp, Willow Spring, NC (US); Darrick Seconi, Cary, NC (US)

(73) Assignee: Icagen, Inc., Durham, NC (US)

( * ) Notice: Subject to any disclaimer, the term of this patent is extended or adjusted under 35 U.S.C. 154(b) by 986 days.

(21) Appl. No.: 11/346,546

(22) Filed: Feb. 1, 2006

(65) Prior Publication Data

US 2006/0178346 A1     Aug. 10, 2006

Related U.S. Application Data

(60) Provisional application No. 60/649,191, filed on Feb. 1, 2005.

(51) Int. Cl.
*A61K 31/13*     (2006.01)
*C07C 249/02*    (2006.01)
(52) U.S. Cl. .................. 514/641; 514/631; 514/633; 514/638; 564/225; 564/229; 564/248; 564/271
(58) Field of Classification Search .................. None
See application file for complete search history.

(56) References Cited

U.S. PATENT DOCUMENTS

| | | | |
|---|---|---|---|
| 5,273,992 A | 12/1993 | Brugnara et al. | |
| 5,358,959 A | 10/1994 | Halperin et al. | |
| 5,441,957 A | 8/1995 | Brugnara et al. | |
| 5,652,236 A | 7/1997 | Krauss | |
| 6,028,123 A | 2/2000 | Hirayama et al. | |
| 6,172,054 B1 | 1/2001 | Clark | |
| 6,172,109 B1 | 1/2001 | Zinke et al. | |
| 6,288,122 B1 | 9/2001 | McNaughton-Smith et al. | |
| 2004/0127464 A1 | 7/2004 | Brugnara et al. | |

FOREIGN PATENT DOCUMENTS

| EP | 0802187 A | 10/1997 |
|---|---|---|
| WO | WO 00/50026 | 8/2000 |

OTHER PUBLICATIONS

Langenegger et al, Helvetica Chimica Acta (2003), 86(10), 3476-3481.*
Benzaquen, et al., "Clotrimazole inhibits cell proliferation in vitro and in vivio," Nature Medicine, 1995, vol. 1 No. 6, pp. 534-540.
Brugnara, et al., "Oral administration of clotrimazole and blockade of human erythrocyte Ca(++)-activated K+ channel: the imidazole ring is not required for inhibitory activity," JPET, 1995, vol. 273 No. 1, pp. 266-272.
Brugnara, et al., "$Ca^{2+}$-Activated $K^+$ Channels of Human and Rabbit Erythrocytes Display Distinctive Patterns of Inhibition by Venom Peptide Toxins," J. Membr. Biol., 1995, vol. 147, pp. 71-82.
Brugnara, C. et al., "Inhibition of $Ca^{2+}$-dependent $K^+$ transport and cell dehydration in sickle erythrocytes by clotrimazole and other imidazole derivatives," J. Clin. Invest., 1993, vol. 92 pp. 520-526.

Brugnara, C. et al., "Therapy with Oral Clotimazole Induces Inhibition of the Gardos Channel and Reduction of Erythrocyte Dehydration in Patients with Sickle Cell Disease," J. Clin. Invest., 1996, vol. 97 No. 5, pp. 1227-1234.
De Franceschi, L. et al., "Treatment with Oral Clotrimazole blocks $Ca^{2+}$-activated $K^+$ transport and reverses Erythrocyte Dehydration in Transgenic SAD mice; *A model for therapy of sickel cell disease*," J. Clin. invest., 1994, vol. 93, pp. 1670-1676.
Do, et al., "Chloride Secretion by Bovine Ciliary Epithelium: a Model of Aqueous Humor Formation ," Investigative Ophthalmology & Visual Sciences, 2000, vol. 41 No. 7, pp. 1853-1860.
Ishii, et al., "A human intermediate conductance calcium-activated potassium channel," Proc. Natl. Acad. Sci., 1997, vol. 94 Issue 21, pp. 11651-11656.
Montero, M. et al., "Agonist-induced $Ca^{2+}$ influx in human neutrophils is secondary to the emptying of intracellular calcium stores.," Biochem. J., 1991, vol. 277, pp. 73-79.
Stuart, et al., "Additive in vetro effect of anti-sickling drugs," British Journal of Haematol. 1994, vol. 86, pp. 820-823.
Villalobos, C. et al., "Inhibition of voltage-gated $Ca^{2+}$ entry into $GH_3$ and chromaffin cells by imidazole antimycotics and other cytochrome P450 blockers ," The FASEB Journal, 1992, vol. 6, pp. 2742-2747.
Zhang, JJ et al., "Three different Cl channels in the bovine ciliary epithelium activated by hypotonic stress ," J. Physiol., 1997, vol. 499 Issue 2, pp. 379-389.
Database CA [Online] Chemical Abstracts Service, Columbus, Ohio, US; Davis, Franklin A. et al: "Asymmetric Synthesis and Properties of Sulfinimines (Thiooxime S-Oxides)" XP002388948 retrieved from STN Database accession No. 1997:218665.
Database CA [Online] Chemical Abstracts Service, Columbus, Ohio, US; Plaquevent, Jean Christophe et al: "Chiral lithium amides. .beta.-Elimination of trityllithium from a lithium amide" XP002388949 retrieved from STN Database accession No. 1989:514787.
Database CA [Online] Chemical Abstracts Service, Columbus, Ohio, US; Grundmann, Christoph et al: "Nitrile oxides. XVI. Dehydro dimers of arylaldoximes as an in situ source of nitrile oxides" XP002388950 retrieved from STN Database accession No. 1973:159503.
Database CA [Online] Chemical Abstracts Service, Columbus, Ohio, US; Curtin, David Y. et al: "Free radical rearrangements. Bis(3,3,3-triphenylpropionyl)diimide,methylazo-2,2,2-triphenylethane, and 2,2,2-triphenylethylhydrazine as radical sources" XP002388951 retrieved from STN Database accession No. 1960:103209.

(Continued)

*Primary Examiner*—Zinna N Davis
(74) *Attorney, Agent, or Firm*—Townsend and Townsend and Crew LLP

(57) ABSTRACT

The present invention provides a class of chemical compounds useful in the treatment of sickle cell disease, diseases characterized by unwanted or abnormal cell proliferation and for the treatment of ocular disorders such as glaucoma. The active compounds are tri-(aryl or heteroaryl) methane compounds or analogues thereof which further comprise an imine moiety and where the tertiary carbon atom can be replaced with a different atom such as Si, Ge, N or P. The compounds enhance resistance to degradation in a biological medium, inhibit potassium flux in a cell, reduce mammalian cell proliferation, reduce the Gardos channel of erythrocytes, reduce sickle erythrocyte dehydration and/or delay the occurrence of erythrocyte sickling or deformation.

13 Claims, No Drawings

OTHER PUBLICATIONS

Database CA [Online] Chemical Abstracts Service, Columbus, Ohio, US; Greene, Janice L. et al: "Chemistry of enolates. II. Selfcondensation of methyl trityl ketone. A novel Claisen condensation" XP002388952 retrieved from STN Database accession No. 1959:11649.

Database CA [Online] Chemical Abstracts Service, Columbus, Ohio, US; Hellerman, Leslie: "Oxidation of compounds possessing the primary amino group. II. 2,2,2-Triphenylethylamine" XP002388953 retrieved from STN Database accession No. 1946:20740.

Database Beilstein Beilstein Institute for Organic Chemistry, Frankfurt-Main, DE; Orechow: XP002388954 Database accession No. 3418032.

Database Beilstein Beilstein Institute for Organic Chemistry, Frankfurt-Main, DE; Wieland, Rosenfeld: XP002388955 Database accession No. 3458762.

Database Beilstein Beilstein Institute for Organic Chemistry, Frankfurt-Main, DE; Nesmejanow et al: XP002388956 Database accession No. 3469860.

Database Beilstein Beilstein Institute for Organic Chemistry, Frankfurt-Main, DE; Orechow, Tiffeneau: XP002388957 Database accession No. 3444641.

Database Beilstein Beilstein Institute for Organic Chemistry, Frankfurt-Main, DE; Curtin, Miller: XP002388958 Database accession No. 6583223.

Database Beilstein Beilstein Institute for Organic Chemistry, Frankfurt-Main, DE; Danilow: XP002388959 Database accession No. 3328853.

Database Beilstein Beilstein Institute for Organic Chemistry, Frankfurt-Main, DE; Curtin, Miller: XP002388960 Database accession No. 2590838.

Database Beilstein Beilstein Institute for Organic Chemistry, Frankfurt-Main, DE; Danilow: XP002388961 Database accession No. 3156095.

Database Beilstein Beilstein Institute for Organic Chemistry, Frankfurt-Main, DE; Hellerman, Gardner: XP002388962 Database accession No. 3328852.

Database Beilstein Beilstein Institute for Organic Chemistry, Frankfurt-Main, DE; Orechow: XP002388963 Database accession No. 33381551.

International Search Report for PCT Application No. PCT/US06/003677 filed on Feb. 1, 2006, 2 pages.

* cited by examiner

IMINES AS ION CHANNEL MODULATORS

CROSS-REFERENCES TO RELATED APPLICATIONS

This application claims priority to U.S. Provisional Application No. 60/649,191, filed Feb. 1, 2005, which is herein incorporated by reference in its entirety for all purposes.

BACKGROUND OF THE INVENTION

Sickle cell disease has been recognized within West Africa for several centuries. Sickle cell anemia and the existence of sickle hemoglobin (Hb S) was the first genetic disease to be understood at the molecular level. It is recognized today as the morphological and clinical result of a glycine to valine substitution at the No. 6 position of the beta globin chain (Ingram, *Nature* 178: 792-794 (1956)). The origin of the amino acid change and of the disease state is the consequence of a single nucleotide substitution (Marotta et al., *J. Biol. Chem.* 252: 5040-5053 (1977)).

The major source of morbidity and mortality of patients suffering from sickle cell disease is vascular occlusion caused by the sickled cells, which causes repeated episodes of pain in both acute and chronic form and also causes ongoing organ damage with the passage of time. It has long been recognized and accepted that the deformation and distortion of sickle cell erythrocytes upon complete deoxygenation is caused by polymerization and intracellular gelation of sickle hemoglobin, hemoglobin S (Hb S). The phenomenon is well reviewed and discussed by Eaton et al., *Blood* 70:1245 (1987). The intracellular gelatin and polymerization of Hb S can occur at any time during an erythrocyte's journey through the vasculature. Thus, erythrocytes in patients with sickle cell disease containing no polymerized hemoglobin S may pass through the microcirculation and return to the lungs without sickling, sickle in the veins, or sickle in the capillaries.

The probability of each of these events is determined by the delay time for intracellular gelation relative to the appropriate capillary transit time (Eaton, et al., *Blood* 47: 621(1976)). In turn, the delay time is dependent upon the oxygenation state of the hemoglobin, with deoxygenation shortening the delay time. If it is thermodynamically impossible for intracellular gelation to take place, or if the delay time at venous oxygen pressures is longer than about 15 seconds, cell sickling will not occur. If the delay time is between about 1 and 15 seconds, the red cell will likely sickle in the veins. If the delay time is less than about 1 second, red cells will sickle within the capillaries.

For red cells that sickle within the capillaries, a number of consequent events are possible. These range from no effect on transit time, to transient occlusion of the capillary, to a more permanent blockage that may ultimately result in ischemia or infarction of the surrounding cells, and in the subsequent destruction of the red cell.

Normal erythrocytes are comprised of approximately 70% water. Water crosses a normal erythrocyte membrane in milliseconds. Loss of cell water causes an exponential increase in cytoplasmic viscosity as the mean cell hemoglobin concentration (MCHC) rises above about 32 g/dL. Since cytoplasmic viscosity is a major determinate of erythrocyte deformability and sickling, the dehydration of the erythrocyte has substantial rheological and pathological consequences. Regulation of erythrocyte dehydration is recognized as an important therapeutic approach for treating sickle cell disease. Since cell water follows any osmotic change in intracellular ion concentration, maintaining the red cell's potassium concentration is of particular importance (Stuart et al., *Brit J Haematol.* 69:1-4 (1988)).

Many approaches to therapeutically treating dehydrated sickle cells (thus decreasing polymerization of hemoglobin S by lowering the osmolality of plasma) have been tried with limited success, including the following approaches: intravenous infusion of distilled water (Gye et al., *Am. J. Med. Sci.* 266: 267-277(1973)); administration of the antidiuretic hormone vasopressin together with a high fluid intake and salt restriction (Rosa et al., *M. Eng. J. Med.* 303:1138-1143 (1980); Charache et al., *Blood* 58: 892-896 (1981)); the use of monensin to increase the cation content of the sickle cell (Clark et al., *J. Clin. Invest.* 70:1074-1080 (1982); Fahim et al., *Life Sciences* 29:1959-1966 (1981)); intravenous administration of cetiedil citrate (Benjamin et al., *Blood* 67: 1442-1447 (1986); Berkowitz et al., *Am. J. Hematol.* 17: 217-223 (1984); Stuart et al., *J. Clin. Pathol.* 40:1182-1186 (1987)); and the use of oxpentifylline (Stuart et al., supra).

Another approach towards therapeutically treating dehydrated sickle cells involves altering erythrocyte potassium flux by targeting a calcium-dependent potassium channel (Ishi et al., *Proc. Natl. Acad. Sci.* 94(21): 11651-11656 (1997)). This calcium activated potassium channel is also referred to as the Gardos channel (Brugnara et al, *J. Clin. Invest.* 92: 520-526 (1993)). Recently, a cloned human intermediate conductance calcium activated potassium channel, hIK1, was shown to be substantially similar to the Gardos channel in terms of both its biophysical and pharmacological properties (Ishi, supra).

Methods that have been used to inhibit the Gardos channel include the administration to erythrocytes of imidazole, nitroimidazole and triazole antimycotic agents such as clotrimazole (U.S. Pat. No. 5,273,992 to Brugnara et al.). Clotrimazole, an imidazole-containing antimycotic agent, has been shown to be a specific, potent inhibitor of the Gardos channel of normal and sickle erythrocytes, and prevents $Ca^{2+}$-dependent dehydration of sickle cells both in vitro and in vivo (Brugnara, supra; De Franceschi et al., *J. Clin. Invest.* 93: 1670-1676 (1994)). When combined with a compound which stabilizes the oxyconformation of Hb S, clotrimazole induces an additive reduction in the clogging rate of a micropore filter and may attenuate the formation of irreversibly sickled cells (Stuart et al., *J. Haematol.* 86:820-823 (1994)). Other compounds that contain a heteroaryl imidazole-like moiety believed to be useful in reducing sickle erythrocyte dehydration via Gardos channel inhibition include miconazole, econazole, butoconazole, oxiconazole and sulconazole. Although these compounds have been demonstrated to be effective at reducing sickle cell dehydration, other imidazole compounds have been found incapable of inhibiting the Gardos channel and preventing loss of potassium.

Since sickle cell anemia is a chronic disease, agents designed for treating it will ideally exhibit certain characteristics that are less essential in drugs for treating resolvable illnesses (e.g., fungal infections). A clinically useful Gardos channel inhibitor will exhibit extremely low toxicity over a prolonged course of administration, will have an excellent bioavailability, will be highly specific for the Gardos channel and will be potent in its interactions with this channel.

As can be seen from the above discussion, reducing sickle erythrocyte dehydration via blockade of the Gardos channel is a powerful therapeutic approach towards the treatment and/or prevention of sickle cell disease. Compounds capable of inhibiting the Gardos channel as a means of reducing sickle cell dehydration are highly desirable, and are therefore an object of the present invention.

Cell proliferation is a normal part of mammalian existence, necessary for life itself. However, cell proliferation is not always desirable, and has recently been shown to be the root of many life-threatening diseases such as cancer, certain skin disorders, inflammatory diseases, fibrotic conditions and arteriosclerotic conditions.

Cell proliferation is critically dependent on the regulated movement of ions across various cellular compartments, and is associated with the synthesis of DNA. Binding of specific polypeptide growth factors to specific receptors in growth-arrested cells triggers an array of early ionic signals that are critical in the cascade of mitogenic events eventually leading to DNA synthesis (Rozengurt, Science 234:161-164 (1986)). These include (1) a rapid increase in cystolic $Ca^{2+}$, mostly due to rapid release of $Ca^{2+}$ from intracellular stores; (2) capacitative $Ca^{2+}$ influx in response to opening of ligand-bound and hyperpolarization-sensitive $Ca^{2+}$ channels in the plasma membrane that contribute further to increased intracellular $Ca^{2+}$ concentration (Tsien and Tsien, Annu. Rev. Cell Biol. 6:715-760 (1990); Peppelenbosch et al., J. Biol. Chem. 266: 19938-19944 (1991)); and (3) activation of $Ca^{2+}$-dependent $K^+$ channels in the plasma membrane with increased $K^+$ conductance and membrane hyperpolarization (Magni et al., J. Biol. Chem. 261:9321-9327 (1991)). These mitogen-induced early ionic changes, considered critical events in the signal transduction pathways, are powerful therapeutic targets for inhibition of cell proliferation in normal and malignant cells.

One therapeutic approach towards the treatment of diseases characterized by unwanted or abnormal cell proliferation via alteration of the ionic fluxes associated with early mitogenic signals involves the administration of clotrimazole. As discussed above, clotrimazole has been shown to inhibit the $Ca^{2+}$-activated potassium channel of erythrocytes. In addition, clotrimazole inhibits voltage- and ligand-stimulated $Ca^{2+}$ influx mechanisms in nucleated cells (Villalobos et al., FASEB J. 6:2742-2747 (1992); Montero et al., Biochem. J. 277:73-79 (1991)) and inhibits cell proliferation both in vitro and in vivo (Benzaquen et al., Nature Medicine 1:534-540 (1995)). Recently, clotrimazole and other imidazole-containing antimycotic agents capable of inhibiting $Ca^{2+}$-activated potassium channels have been shown to be useful in the treatment of arteriosclerosis (U.S. Pat. No. 5,358,959 to Halperin et al.), as well as other disorders characterized by unwanted or abnormal cell proliferation.

Glaucoma is a disease characterized by increased intraocular pressure. Increased intraocular pressure is associated with many diseases including, but not limited to, primary open-angle glaucoma, normal tension glaucoma, angle-closure glaucoma, acute glaucoma, pigmentary glaucoma, neovascular glaucoma, or trauma related glaucoma, Sturge-Weber syndrome, uveitis, and exfoliation syndrome.

Currently, there are a variety of drugs available that employ different mechanisms to lower intraocular pressure, e.g., timolol, betaxolol, levobunolol, acetazolamide, methazolamide, dichlorphenamide, dorzolamide, brinzolamide, latanoprost, brimonidine, and bimatoprost (see, e.g., U.S. Pat. No. 6,172,054, U.S. Pat. No. 6,172,109, and U.S. Pat. No. 5,652, 236). Miotics, beta blockers, alpha-2 agonists, carbonic anhydrase inhibitors, beta adrenergic blockers, prostaglandins and docosanoid are all currently used alone or in combination to treat glaucoma. Miotics and prostaglandins are believed to lower intraocular pressure by increasing drainage of the intraocular fluid, while beta blockers, alpha-2 agonists and carbonic anhydrase are believed to lower intraocular pressure by decreasing production of intraocular fluid thereby reducing the flow of fluid into the eye. All are characterized by side effects ranging from red eye and blurring of vision to decreased blood pressure and breathing difficulties.

BRIEF SUMMARY OF THE INVENTION

Reducing sickle erythrocyte dehydration via blockade of the Gardos channel is a powerful therapeutic approach towards the treatment and/or prevention of sickle cell disease. Compounds capable of inhibiting the Gardos channel as a means of reducing sickle cell dehydration are highly desirable, and are an object of the present invention. Although of demonstrable efficacy, the imidazole-based Gardos channel inhibitors that have been explored to date are hampered by several shortcomings including a well-documented potential for hepatotoxicity. This toxicity is exacerbated by the inhibitors' low potencies, non-specific interactions with calcium activated potassium channels other than the Gardos channel and low bioavailabilities, each of which motivate for the administration of higher and more frequent dosages of the inhibitors.

Cell proliferation is a normal part of mammalian existence, necessary for life itself. However, cell proliferation is not always desirable, and has recently been shown to be the root of many life-threatening diseases such as cancer, certain skin disorders, inflammatory diseases, fibrotic conditions and arteriosclerotic conditions.

Glaucoma is a disease characterized by increased intraocular pressure. Increased intraocular pressure is associated with many diseases including, but not limited to, primary open-angle glaucoma, normal tension glaucoma, angle-closure glaucoma, acute glaucoma, pigmentary glaucoma, neovascular glaucoma, or trauma related glaucoma, Sturge-Weber syndrome, uveitis, and exfoliation syndrome.

Currently, there are a variety of drugs available that employ different mechanisms to lower intraocular pressure, e.g., timolol, betaxolol, levobunolol, acetazolamide, methazolamide, dichlorphenamide, dorzolamide, brinzolamide, latanoprost, brimonidine, and bimatoprost (see, e.g., U.S. Pat. No. 6,172,054, U.S. Pat. No. 6,172,109, and U.S. Pat. No. 5,652, 236). Miotics, beta blockers, alpha-2 agonists, carbonic anhydrase inhibitors, beta adrenergic blockers, prostaglandins and docosanoid are all currently used alone or in combination to treat glaucoma. Miotics and prostaglandins are believed to lower intraocular pressure by increasing drainage of the intraocular fluid, while beta blockers, alpha-2 agonists and carbonic anhydrase are believed to lower intraocular pressure by decreasing production of intraocular fluid thereby reducing the flow of fluid into the eye. All are characterized by side effects ranging from red eye and blurring of vision to decreased blood pressure and breathing difficulties.

Thus, in a first aspect, the present invention provides a compound having a structure according to Formula (I):

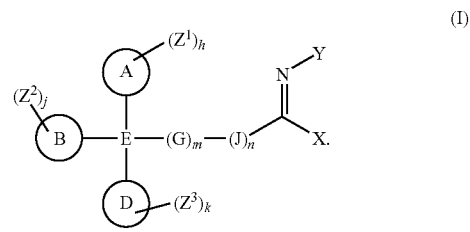

The rings A, B, and D are independently selected from substituted or unsubstituted aryl, and substituted or unsubstituted heteroaryl. E is C, P, Si, or Ge. G is substituted or unsubstituted alkylene, or substituted or unsubstituted heteroalkylene. J is $-N(R^1)-$, $-O-$, or $-S-$.

X is H, substituted or unsubstituted alkyl, $-NR^2R^3$, $SR^{4a}$, or $-OR^{5a}$. Y is $-R^6$, $-OR^7$, or $-NR^8R^9$.

The ring substituents $Z^1$, $Z^2$, and $Z^3$ are independently H, hydroxyl, amino, cyano, nitro, halogen, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, $-SR^{4b}$, $-OR^{5b}$, $-P(O)R^{10a}R^{11a}$, $-S(O)_{q1}R^{12a}R^{13a}$, $-S(O)_{q1}R^{12a}$, $-NR^{14}R^{15}$, $-N(R^{14})C(O)R^{15}$, $-C(O)R^{15}$, $-C(O)NR^{14}R^{15}$, or $-PR^{14}R^{15}$. The symbol q1 represents the integers 1 or 2.

The symbols h, j, and k are integers independently selected from 0, 1, 2, 3, 4, and 5. The symbols m and n are integers independently selected from 0 and 1.

$R^1$ is selected from H, amino, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, $-P(O)R^{10b}R^{11b}$, $-S(O)_{q2}R^{12b}R^{13b}$, $S(O)_{q2}R^{12b}$, and $-C(O)R^{17a}$. The symbol q2 is an integer selected from 1 and 2.

$R^2$ is selected from H, hydroxyl, amino, substituted or unsubstituted alkyl, substituted or unsubstituted cycloalkyl, substituted or unsubstituted heteroalkyl, substituted or unsubstituted heterocycloalkyl, substituted or unsubstituted aryl, and substituted or unsubstituted heteroaryl. $R^3$ is selected from H, hydroxyl, amino, substituted or unsubstituted alkyl, substituted or unsubstituted cycloalkyl, substituted or unsubstituted heteroalkyl, substituted or unsubstituted heterocycloalkyl, substituted or unsubstituted aryl, and substituted or unsubstituted heteroaryl, $-P(O)R^{10c}R^{11c}$, $-S(O)_{q3}R^{12c}$, $(O)_{q3}R^{12c}R^{13c}$, or $-C(O)R^{17b}$. The symbol q3 is an integer selected from 1 and 2. $R^2$ and $R^3$ are optionally joined to form a substituted or unsubstituted heterocycloalkyl or substituted or unsubstituted heteroaryl with the nitrogen to which they are attached.

$R^{4a,b}$ (i.e. $R^{4a}$ and $R^{4b}$) are independently selected from H, substituted or unsubstituted alkyl, substituted or unsubstituted cycloalkyl, substituted or unsubstituted heteroalkyl, substituted or unsubstituted heterocycloalkyl, substituted or unsubstituted aryl, and substituted or unsubstituted heteroaryl. $R^{5a,b}$ are independently selected from H, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, $-P(O)R^{10d}R^{11d}$, $-S(O)_{q4}R^{12d}$, and $-S(O)_{q4}R^{12d}R^{13d}$. The symbol q4 is an integer selected from 1 and 2.

$R^6$ is selected from H, cyano, $-NO_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $-P(O)R^{10e}R^{11e}$, $-S(O)_{q5}R^{12e}$, and $S(O)_{q5}R^{12e}R^{13e}$. The symbol q5 is an integer selected from 1 and 2.

$R^7$ is selected from H, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, $-C(O)R^{10f}$, and $-P(O)R^{10f}R^{11f}$. $R^8$ is selected from H, substituted or unsubstituted alkyl, substituted or unsubstituted cycloalkyl, substituted or unsubstituted heteroalkyl, and substituted or unsubstituted heterocycloalkyl, substituted or unsubstituted aryl, and substituted or unsubstituted heteroaryl. $R^9$ is H, $-OH$, CN, nitro, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, $-P(O)R^{10g}R^{11g}$, $-S(O)_{q6}R^{12f}$, $-S(O)_{q6}R^{12f}R^{13f}$, or $-C(O)R^{17c}$. The symbol q6 is an integer selected from 1 and 2. $R^8$ and $R^9$ are optionally joined to from a substituted or unsubstituted heterocycloalkyl or substituted or unsubstituted heteroaryl with the nitrogen to which they are attached.

$R^{10a,b,c,d,e,f}$ and $R^{11a,b,c,d,e,f}$ are independently selected from, amino, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, and $-OR^{16}$. $R^{16}$ is independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, $R^{16}$ is independently hydrogen or substituted or unsubstituted $C_1$-$C_{10}$ alkyl. For each $R^{10}/R^{11}$ pair, only one of $R^{10}$ and $R^{11}$ may be amino. Thus, $R^{11a}$ and $R^{11a}$, $R^{11b}$ and $R^{11b}$, $R^{10c}$ and $R^{11c}$, $R^{10d}$ and $R^{11d}$, $R^{10e}$ and $R^{11e}$, $R^{10f}$ and $R^{11f}$, and $R^{10g}$ and $R^{11g}$ are not simultaneously amino.

$R^{12a,b,c,d,e,f,g}$ and $R^{13a,b,c,d,e,f,g}$ are independently selected from amino, substituted or unsubstituted alkyl, substituted or unsubstituted cycloalkyl, substituted or unsubstituted heteroalkyl, substituted or unsubstituted heterocycloalkyl, substituted or unsubstituted aryl, and substituted or unsubstituted heteroaryl.

$R^{14}$ and $R^{15}$ are independently selected from substituted or unsubstituted alkyl, substituted or unsubstituted cycloalkyl, substituted or unsubstituted heteroalkyl, substituted or unsubstituted heterocycloalkyl, substituted or unsubstituted aryl, and substituted or unsubstituted heteroaryl.

$R^{17a,b,c}$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, and $-OR^{18}$. $R^{18}$ is independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

Y and X, together with the atoms to which they are attached, are optionally joined to form a substituted or unsubstituted membered ring (e.g. a 5- to 7-membered ring). $Z^1$ and X, together with the atoms to which they are attached, are optionally joined to form a bicyclic fused ring. $Z^3$ and X, together with the atoms to which they are attached, are optionally joined to form a bicyclic fused ring. $Z^1$ and $Z^2$, together with the atoms to which they are attached, are optionally joined to form a tricyclic fused ring. $Z^1$ and $Z^3$, together with the atoms to which they are attached, are optionally joined to form a tricyclic fused ring. $Z^2$ and $Z^3$, together with the atoms to which they are attached, are optionally joined to form a tricyclic fused ring.

The present invention also provides compounds having a structure according to Formula (II):

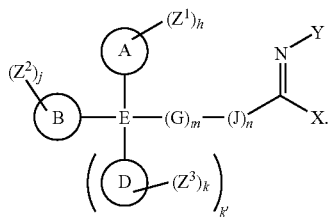

In Formula (II), $Z^1$, $Z^2$, $Z^3$, h, j, k, A, B, D, G, J, m, n, Y, and X are as defined above in the discussion of Formula (I).

E is selected from C, P, Si, Ge, $N^+$, and N. The symbol k' represents an integer selected from 0 and 1. Where E is C, P, Si, Ge, or $N^+$, k' is 1. Where E is N, k' is 0. One of skill in that art will recognize that any appropriate counter ion (e.g. a negatively charged compound of element) may be present where E is $N^+$.

In a second aspect, the invention provides pharmaceutical compositions comprising a compound of Formulae (I) or (II) in admixture with a pharmaceutically acceptable excipient.

Controlling diseases (e.g., sickle cell disease) via altering cellular ionic fluxes of cells affected by a disease is a powerful therapeutic approach. Moreover, basic understanding of the role of cellular ionic fluxes in both disease processes and normal physiology promises to provide new therapeutic modalities, regimens and agents. Compounds that alter cellular ion fluxes, particularly those that inhibit potassium flux, are highly desirable as both drugs and as probes for elucidating the basic mechanisms underlying these ion fluxes. Similarly, methods utilizing these compounds in basic research and in therapeutic applications are valuable tools in the arsenal of both the researcher and clinician. Therefore such compounds and methods are also an object of the present invention.

Thus, in a third aspect, the invention provides a method of inhibiting potassium flux of a cell. In this method, a cell is contacted with an effective amount of a compound of Formulae (I) or (II).

An important therapeutic pathway for treatment of sickle cell disease is preventing or retarding the dehydration of erythrocytes by manipulating the cellular ion fluxes of erythrocytes. Thus, in a fourth aspect, the invention provides a method for reducing erythrocyte dehydration. The method comprises contacting an erythrocyte with an amount of a compound of Formulae (I) or (II) effective to reduce erythrocyte dehydration.

In a fifth aspect, the invention provides a method of treating or preventing sickle cell disease. The method comprises administering to a subject suffering sickle cell disease a therapeutically effective amount of a compound of Formulae (I) or (II).

In a sixth aspect, the invention provides a method for enhancing resistance of a potassium channel inhibitor to degradation in a biological medium. The method comprises substituting a radical comprising a fluorine atom for a hydrogen atom on the aryl radical of the inhibitor. The potassium channel inhibitor in this aspect comprises a imine moiety and a phenyl moiety.

In a seventh aspect, the invention provides a method of inhibiting mammalian cell proliferation. This method comprises the step of contacting a mammalian cell with an effective amount of a compound of Formulae (I) or (II).

In an eighth aspect, the invention provides a method of treating a disorder characterized by abnormal cell proliferation. This method comprises the step of administering to a subject a therapeutically effective amount of a composition having a compound of Formulae (I) or (II).

The present invention also relates to the use of compounds able to decrease potassium ion flow through IK1 channels for the treatment of diseases related to increased intraocular pressure modulated by potassium channels. In one aspect, the invention provides a method for reducing intraocular pressure in a subject in need thereof. Intraocular pressure is reduced by decreasing potassium ion flow through IK1 channels in a cell, e.g., a cell capable of mediating the production and/or secretion of aqueous humor. A method for reducing intraocular pressure, therefore, includes treatment methods for subjects in need thereof by administering to a subject a pharmaceutically acceptable carrier and at least one compound able to decrease potassium ion flow through IK1 channels. The composition is administered to the subject in a potassium ion flow decreasing amount.

In one embodiment of the invention, the subject has glaucoma characterized by increased intraocular pressure. In one aspect of the invention, the method prevents glaucoma characterized by increased intraocular pressure. In another aspect of the invention the glaucoma is primary open-angle glaucoma, normal tension glaucoma, angle-closure glaucoma, acute glaucoma, pigmentary glaucoma, neovascular glaucoma, or trauma related glaucoma.

In one embodiment of the invention, the glaucoma is hereditary. In another embodiment, the glaucoma is non-hereditary.

In one aspect of the invention, the subject has increased intraocular pressure associated with Sturge-Weber syndrome. In one embodiment of the invention, the method prevents increased intraocular pressure associated with Sturge-Weber syndrome.

In another aspect of the invention, the subject has increased intraocular pressure associated with uveitis. In yet another aspect of the invention, the method reduces intraocular pressure to between 12 and 20 mm of mercury. In one embodiment, the method maintains intraocular pressure between 12 and 20 mm of mercury.

In one aspect of the invention, the compound treats chronic elevation of intraocular pressure. In another aspect, it treats acute elevation of intraocular pressure. In yet another aspect of the invention, the compound treats gradual elevation of intraocular pressure.

In another aspect, the invention provides treatment methods for diseases of the eye characterized by increased intraocular pressure.

In one embodiment of the invention, the method prevents destruction of optic nerve cells. In one aspect, the method prevents atrophy of optic nerve cells. In another aspect, the method prevents blindness.

In another embodiment of the invention, the compound treats exfoliation syndrome characterized by increased intraocular pressure. In yet another embodiment, the compound inhibits aqueous humor secretion.

In one aspect of the invention, the subject is a human.

In another aspect of the invention, the IK1 potassium channel is a homomeric channel.

In one embodiment of the invention, the potassium ion flow decreasing amount is 0.001% to 10% w/v. In another embodiment, the potassium flow decreasing amount is 0.1% to 5% w/v. In another embodiment, the potassium ion flow decreasing amount is 10-1000.mu.g per eye. In another embodiment, the potassium ion flow decreasing amount is 75-150.mu.g per eye.

In one aspect of the invention, the composition is administered topically.

Another aspect of the invention includes the step of administering to a subject a second or multiple therapeutic agent(s) known to reduce intraocular pressure in a subject. Said agent(s) may be administered with a IK1 inhibitor of the present invention in a single pharmaceutical formulation or as multiple pharmaceutical formulations admixed into a single formulation for ultimate administration to a patient. Suitable intraocular-lowering agents include one or more compounds selected from the group consisting of miotics, sympathomimetics, beta-blockers, alpha-2 agonists, carbonic anhydrase inhibitors, and prostaglandins. Examples of such compounds include timolol, betaxolol, levobunolol, acetazolamide, methazolamide, dichlorphenamide, dorzolamide, brinzolamide, latanoprost, brimonidine, and bimatoprost.

Another aspect of the invention includes the step of administering to the subject a second pharmaceutical composition known to reduce intraocular pressure in a subject. In one embodiment, the second pharmaceutical composition includes as its active ingredient one or more compounds selected from the group consisting of miotics, sympathomimetics, beta-blockers, alpha-2 agonists, carbonic anhydrase inhibitors, and prostaglandins. Examples of such compounds include timolol, betaxolol, levobunolol, acetazolamide, methazolamide, dichlorphenamide, dorzolamide, brinzolamide, latanoprost, brimonidine, and bimatoprost.

These and other objects and advantages of the present invention will be apparent from the detailed description and examples that follow.

DETAILED DESCRIPTION OF THE INVENTION

I. Introduction

As discussed above, blockade of sickle dehydration via inhibition of the Gardos channel is a powerful therapeutic approach for the treatment and/or prevention of sickle cell disease. In vitro studies have shown that clotrimazole, an imidazole-containing antimycotic agent, blocks $Ca^{2+}$-activated $K^+$ flux and cell dehydration in sickle erythrocytes (Brugnara et al., *J. Clin. Invest.* 92: 520-526 (1993)). Studies in a transgenic mouse model for sickle cell disease, SAD-1 mouse (Trudel et al., *EMBO J.* 11: 3157-3165 (1991)), show that oral administration of clotrimazole leads to inhibition of the red cell Gardos channel, increased red cell $K^+$ content, a decreased mean corpuscular hemoglobin concentration (MCHC) and decreased cell density (De Franceschi et al., *J. Clin. Invest.* 93: 1670-1676 (1994)). Moreover, therapy with oral clotrimazole induces inhibition of the Gardos channel and reduces erythrocyte dehydration in patients with sickle cell disease (Brugnara et al., *J. Clin. Invest.* 97: 1227-1234 (1996)). Other antimycotic agents, which inhibit the Gardos channel in vitro, include miconazole, econazole butoconazole, oxiconazole and sulconazole (U.S. Pat. No. 5,273,992 to Brugnara et al.). All of these compounds contain an imidazole-like ring. i.e., a heteroaryl ring containing two or more nitrogens.

Also as discussed in the Background section, the modulation of early ionic mitogenic signals and inhibition of cell proliferation are powerful therapeutic approaches towards the treatment and/or prevention of disorders characterized by abnormal cell proliferation. It has been shown that clotrimazole, in addition to inhibiting the Gardos channel of erythrocytes, also modulates ionic mitogenic signals and inhibits cell proliferation both in vitro and in vivo.

For example, clotrimazole inhibits the rate of cell proliferation of normal and cancer cell lines in a reversible and dose-dependent manner in vitro (Benzaquen et al., *Nature Medicine* 1:534-540 (1995)). Clotrimazole also depletes the intracellular $Ca^{2+}$ stores and prevents the rise in cystolic $Ca^{2+}$ that normally follows mitogenic stimulation. Moreover, in mice with severe combined immunodeficiency disease (SCID) and inoculated with MM-RU human melanoma cells, daily administration of clotrimazole resulted in a significant reduction in the number of lung metastases observed (Benzaquen et al., supra).

Although of demonstrable efficacy, the imidazole-based Gardos channel inhibitors that have been explored to date are hampered by several shortcomings including a well-documented potential for hepatotoxicity. This toxicity is exacerbated by the inhibitors' low potencies, non-specific interactions with potassium channels other than the Gardos channel and low bioavailabilities, each of which motivate for the administration of higher and more frequent dosages of the inhibitors. Thus, in one aspect, the present invention provides a new class of organic compounds that are capable of inhibiting the $Ca^{2+}$-activated potassium channel (Gardos channel) or erythrocytes, particularly sickle erythrocytes and/or of inhibiting mammalian cell proliferation, particularly mitogen-induced cell proliferation. These compounds have increased potency and bioavailability, as well as reduced non-specific interactions, over the imidazole-based Gardos-channel inhibitors that have been explored to date.

In another aspect, the invention provides a method of reducing sickle cell dehydration and/or delaying the occurrence of erythrocyte sickling in situ as a therapeutic approach towards the treatment of sickle cell disease. In its broadest sense, the method involves only a single step—the administration of at least one pharmacologically active compound of the invention, or a composition thereof, to a sickle erythrocyte in situ in an amount effective to reduce dehydration and/or delay the occurrence of cell sickling or deformation.

While not intending to be bound by any particular theory, it is believed that administration of the active compounds described herein in appropriate amounts to sickle erythrocytes in situ causes reduction (in some cases nearly complete inhibition) of ion flow through the Gardos channel of sickle cells, thereby reducing the dehydration of sickle cells and/or delaying the occurrence of cell sickling or deformation. In a some embodiments, the dehydration of a sickle cell is reduced and/or the occurrence of sickling is delayed in a sickle cell that is within the microcirculation vasculature of the subject, thereby reducing or eliminating the vaso-occlusion that is commonly caused by sickled cells.

The invention is also directed to methods of treating or preventing sickle cell disease. In the method, an effective amount of one or more compounds according to the invention, or a pharmaceutical composition thereof, is administered to a patient suffering from sickle cell disease. The methods may be used to treat sickle cell disease prophylactically to decrease intracellular Hb S concentration and/or polymerization, and thus diminish the time and duration of red cell sickling and vaso-occlusion in the blood circulation. The methods may also be used therapeutically in patients with acute sickle cell crisis, and in patients suffering chronic sickle cell episodes to control both the frequency and duration of the crises.

The compounds of the invention are also potent, specific inhibitors of mammalian cell proliferation. Thus, in another aspect, the invention provides methods of inhibiting mammalian cell proliferation as a therapeutic approach towards the treatment or prevention of diseases characterized by unwanted or abnormal cell proliferation. In its broadest sense, the method involves the administration of an effective amount of at least one pharmacologically active compound according to the invention to a mammalian cell in situ. The compound may act, for example, cytostatically, cytotoxically, or by a combination of both mechanisms to inhibit cell proliferation. Mammalian cells treatable in this manner include vascular smooth muscle cells, fibroblasts, endothelial cells, various pre-cancer cells and various cancer cells. In a some embodiments, cell proliferation is inhibited in a subject suffering from a disorder that is characterized by unwanted or abnormal cell proliferation. Such diseases are described more fully below.

The invention is also directed to methods of treating or preventing diseases characterized by abnormal cell proliferation. In the method, an effective amount of at least one compound according to the invention, or a pharmaceutical composition thereof, is administered to a patient suffering from a disorder that is characterized by abnormal cell proliferation. While not intending to be bound by any particular theory, it is believed that administration of an appropriate amount of a compound according to the invention to a subject decreases (e.g. inhibits) cell proliferation by altering the ionic fluxes associated with early mitogenic signals. Such alteration of ionic fluxes is thought to be due to the ability of the compounds of the invention to inhibit potassium channels of cells, particularly $Ca^{2+}$-activated potassium channels. The method can be used prophylactically to prevent unwanted or abnormal cell proliferation, or may be used therapeutically to reduce or arrest proliferation of abnormally proliferating cells. The compound, or a pharmaceutical formulation thereof, can be applied locally to proliferating cells to arrest or inhibit proliferation at a desired time, or may be administered to a subject systemically to arrest or inhibit cell proliferation.

Diseases which are characterized by abnormal cell proliferation that can be treated or prevented by means of the present invention include blood vessel proliferative disorders, fibrotic disorders, arteriosclerotic disorders and various cancers.

Blood vessel proliferation disorders refer to angiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing and organ regeneration. They also play a pivotal role in cancer development. Other examples of blood vessel proliferative disorders include arthritis, where new capillary blood vessels invade the joint and destroy cartilage and ocular diseases such as diabetic retinopathy, where new capillaries in the retina invade the vitreous, bleed and cause blindness and neovascular glaucoma.

Another example of abnormal neovascularization is that associated with solid tumors. It is now established that unrestricted growth of tumors is dependent upon angiogenesis and that induction of angiogenesis by liberation of angiogenic factors can be an important step in carcinogenesis. For example, basic fibroblast growth factor (bFGF) is liberated by several cancer cells and plays a crucial role in cancer angiogenesis. The demonstration that certain animal tumors regress when angiogenesis is inhibited has provided the most compelling evidence for the role of angiogenesis in tumor growth. Other cancers that are associated with neovascularization include hemangioendotheliomas, hemangiomas and Kaposi's sarcoma.

Proliferation of endothelial and vascular smooth muscle cells is the main feature of neovascularization. The invention is useful in inhibiting such proliferation, and therefore in inhibiting or arresting altogether the progression of the angiogenic condition which depends in whole or in part upon such neovascularization. The invention is particularly useful when the condition has an additional element of endothelial or vascular smooth muscle cell proliferation that is not necessarily associated with neovascularization. For example, psoriasis may additionally involve endothelial cell proliferation that is independent of the endothelial cell proliferation associated with neovascularization. Likewise, a solid tumor which requires neovascularization for continued growth may also be a tumor of endothelial or vascular smooth muscle cells. In this case, growth of the tumor cells themselves, as well as the neovascularization, is inhibited by the compounds described herein.

The invention is also useful for the treatment of fibrotic disorders such as fibrosis and other medical complications of fibrosis which result in whole or in part from the proliferation of fibroblasts. Medical conditions involving fibrosis (other than atherosclerosis, discussed below) include undesirable tissue adhesion resulting from surgery or injury.

Other cell proliferative disorders which can be treated by means of the invention include arteriosclerotic conditions. Arteriosclerosis is a term used to describe a thickening and hardening of the arterial wall. An arteriosclerotic condition as used herein means classical atherosclerosis, accelerated atherosclerosis, atherosclerotic lesions and any other arteriosclerotic conditions characterized by undesirable endothelial and/or vascular smooth muscle cell proliferation, including vascular complications of diabetes.

Proliferation of vascular smooth muscle cells is a main pathological feature in classical atherosclerosis. It is believed that liberation of growth factors from endothelial cells stimulates the proliferation of subintimal smooth muscle which, in turn, reduces the caliber and finally obstructs the artery. The invention is useful in decreasing (e.g. inhibiting) such proliferation, and therefore in delaying the onset of, delaying the progression of (e.g. halting the progression) such proliferation and the associated atherosclerotic condition.

Proliferation of vascular smooth muscle cells produces accelerated atherosclerosis, which is the main reason for failure of heart transplants that are not rejected. This proliferation is also believed to be mediated by growth factors, and can ultimately result in obstruction of the coronary arteries. The invention is useful in decreasing (e.g. inhibiting) such obstruction and reducing the risk of, or even preventing, such failures.

Vascular injury can also result in endothelial and vascular smooth muscle cell proliferation. The injury can be caused by any number of traumatic events or interventions, including vascular surgery and balloon angioplasty. Restenosis is the main complication of successful balloon angioplasty of the coronary arteries. It is believed to be caused by the release of growth factors as a result of mechanical injury to the endothelial cells lining the coronary arteries. Thus, by decreasing unwanted endothelial and smooth muscle cell proliferation, the compounds described herein can be used to delay, or even avoid, the onset of restenosis.

Other atherosclerotic conditions which can be treated or prevented by means of the present invention include diseases of the arterial walls that involve proliferation of endothelial and/or vascular smooth muscle cells, such as complications of diabetes, diabetic glomerulosclerosis and diabetic retinopathy.

The compounds described herein are also useful in treating or preventing various types of cancers. Cancers which can be treated by means of the present invention include, but are not limited to, biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute and chronic lymphocytic and myelogenous leukemia, multiple myeloma, AIDS associated leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma (teratomas, choriocarcinomas)), stromal tumors and germ cell tumors; thyroid cancer, including thyroid adenocarcinoma and medullar carcinoma; and renal cancer including adenocarcinoma and Wilms tumor.

The compounds of the invention are useful with hormone dependent and also with nonhormone dependent cancers. They also are useful with prostate and nonprostate cancers and with breast and nonbreast cancers. They further are useful with multidrug resistant strains of cancer.

In addition to the particular disorders enumerated above, the invention is also useful in treating or preventing dermatological diseases including keloids, hypertrophic scars, seborrheic dermatosis, papilloma virus infection (e.g., producing verruca vulgaris, verruca plantaris, condylomata, etc.), eczema and epithelial precancerous lesions such as actinic keratosis; other inflammatory diseases including proliferative glomerulonephritis; lupus erythematosus; scleroderma; temporal arthritis; thromboangiitis obliterans; mucocutaneous lymph node syndrome; and other pathologies mediated by growth factors including uterine leiomyomas.

The present invention also relates to the use of compounds of the present invention to decrease potassium ion flow through IK1 channels for the treatment of diseases related to increased intraocular pressure modulated by potassium channels.

In one aspect, the invention provides a method for reducing intraocular pressure in a subject in need thereof. Intraocular pressure is reduced by decreasing potassium ion flow through IK1 channels in a cell, e.g., a cell capable of mediating the production and/or secretion of aqueous humor. A method for reducing intraocular pressure, therefore, includes treatment methods for subjects in need thereof by administering to a subject a pharmaceutically acceptable carrier and at least one compound able to decrease potassium ion flow through IK1 channels. The composition is administered to the subject in a potassium ion flow decreasing amount.

In one embodiment of the invention, the subject is afflicted with glaucoma characterized by increased intraocular pressure. In one aspect of the invention, the method prevents or reduces glaucoma characterized by increased intraocular pressure. In another aspect of the invention the glaucoma is primary open-angle glaucoma, normal tension glaucoma, angle-closure glaucoma, acute glaucoma, pigmentary glaucoma, neovascular glaucoma, or trauma related glaucoma.

In one embodiment of the invention, the glaucoma is hereditary. In another embodiment, the glaucoma is non-hereditary.

In one aspect of the invention, the subject has increased intraocular pressure associated with Sturge-Weber syndrome. In one embodiment of the invention, the method prevents or treats increased intraocular pressure associated with Sturge-Weber syndrome.

In another aspect of the invention, the subject has increased intraocular pressure associated with uveitis.

In yet another aspect of the invention, the method reduces intraocular pressure to between 12 and 20 mm of mercury. In one embodiment, the method maintains intraocular pressure between 12 and 20 mm of mercury.

In one aspect of the invention, the compound treats chronic elevation of intraocular pressure. In another aspect, it treats acute elevation of intraocular pressure. In yet another aspect of the invention, the compound treats gradual elevation of intraocular pressure.

In another aspect, the invention provides treatment methods for diseases of the eye characterized by increased intraocular pressure.

In one embodiment of the invention, the method prevents or reduces destruction of optic nerve cells. In one aspect, the method prevents or treats atrophy of optic nerve cells. In another aspect, the method prevents or treats blindness.

In another embodiment of the invention, the compound treats exfoliation syndrome characterized by increased intraocular pressure. In yet another embodiment, the compound reduces or inhibits aqueous humor secretion.

In one aspect of the invention, the subject is a human.

In another aspect of the invention, the IK1 potassium channel is a homomeric channel.

In one embodiment of the invention, the potassium ion flow decreasing amount is 0.001% to 10% w/v. In another embodiment, the potassium flow decreasing amount is 0.1% to 5% w/v. In another embodiment, the potassium ion flow decreasing amount is 10-1000 µg per eye. In another embodiment, the potassium ion flow decreasing amount is 75-150 µg per eye.

In one aspect of the invention, the composition is administered topically.

Another aspect of the invention includes the step of administering to a subject a second or multiple therapeutic agent(s) known to reduce intraocular pressure in a subject. Said agent(s) may be administered with a IK1 inhibitor of the present invention in a single pharmaceutical formulation or as multiple pharmaceutical formulations admixed into a single formulation for ultimate administration to a patient. Suitable intraocular-lowering agents include one or more compounds selected from the group consisting of miotics, sympathomimetics, beta-blockers, alpha-2 agonists, carbonic anhydrase inhibitors, and prostaglandins. Examples of such compounds include timolol, betaxolol, levobunolol, acetazolamide, methazolamide, dichlorphenamide, dorzolamide, brinzolamide, latanoprost, brimonidine, and bimatoprost.

Another aspect of the invention includes the step of administering to the subject a second pharmaceutical composition known to reduce intraocular pressure in a subject. In one embodiment, the second pharmaceutical composition includes as its active ingredient one or more compounds selected from the group consisting of miotics, sympathomimetics, beta-blockers, alpha-2 agonists, carbonic anhydrase inhibitors, and prostaglandins. Examples of such compounds include timolol, betaxolol, levobunolol, acetazolamide, methazolamide, dichlorphenamide, dorzolamide, brinzolamide, latanoprost, brimonidine, and bimatoprost.

The present invention provides a mechanism for treating diseases related to increased intraocular pressure and provides assays for identifying compounds that inhibit IK1 channels and reduce intraocular pressure. Modulation of IK1 channels therefore represents a novel approach to the treatment of diseases related to increased intraocular pressure. Modulation of IK1 channels can be useful for the treatment of increased intraocular pressure associated with diseases such as glaucoma, Sturge Weber syndrome, exfoliation syndrome, and uveitis. It can also be useful for treating gradual, chronic, and acute elevation of intraocular pressure as well as for preventing the atrophy and destruction of optic nerve cells.

In this invention, compounds able to decrease potassium ion flow through IK1 channels are used to treat increased intraocular pressure. The IK1 channel has been implicated in maintaining ion homeostasis during secretion in a variety of epithelial cells. (Zhang et al., *J. Physiol.* 499.2:379-389 (1997), Do et al., *Invest Ophthalmol Vis. Sci.* 41:1853-60 (2000)) However, before the present invention, it was not known that IK1 channels are involved in modulating intraocular pressure.

Aqueous humor, a watery fluid responsible for nourishing the eye and for maintaining intraocular pressure, is secreted by the ciliary epithelium. Current flow across the epithelium regulates the rate of secretion. (Zhang et al., *J. Physiol.* 499.2: 379-389 (1997), Do et al., *Invest Ophthalmol Vis. Sci.* 41:1853-60 (2000)). The present invention provides methods of treating increased intraocular pressure by administering to subjects compounds able to block IK1 channels. Without being bound by a particular theory, IK1 channels are thought to decrease levels of secretion from the ciliary body. Decreased secretion leads to decreased production of aqueous humor and a corresponding decrease in intraocular pressure. Alternatively, in many patients suffering from diseases related to increased intraocular pressure, the eye is unable to drain the intraocular fluid, creating a buildup of aqueous humor within the anterior chamber of the eye.

In one example, the effect of compounds that decrease potassium ion flow through IK1 channels are tested in vivo in normotensive rabbits. Rabbits are administered an ocular suspension containing a compound of the present invention. Intraocular pressure and pupil diameter measurements are taken. The rabbits to which a compound of the present invention are given display a significant decrease in intraocular pressure. In this assay, the rabbits show at least a 2-4 mm decrease in Hg pressure, preferably greater than a 5 mm decrease in Hg pressure.

This assay demonstrates that administration of an IK1 channel blocker can reduce intraocular pressure in a subject animal. Thus, IK1 channel inhibitors can be used to treat diseases related to increased intraocular pressure. Such modulators are identified using the in vitro and in vivo assays described herein (see, e.g., WO 00/50026, U.S. Pat. Nos. 6,288,122, 6,028,123, 5,441,957, and 5,273,992; see also Brugnara et al., *J. Clin. Invest.* 92:520-526 (1993)). In another embodiment, the invention uses an in vitro CHO cell assay, wherein the CHO cells express recombinant IK1, with measurement of radiolabeled rubidium flux as described, e.g., in Brugnara et al., *J. Clin. Invest.* 92:520-526 (1993). In another embodiment, the compounds of the invention are tested using a in vivo normotensive mammal, e.g., rabbit, assay, described above.

II. Abbreviations and Definitions

As used herein, the singular form "a", "an" and "the" include plural referents unless the context clearly dictates otherwise. Thus, for example, reference to "a fusion protein" includes a plurality of proteins and reference to "an oxime compound" includes a plurality of compounds and the like.

Unless defined otherwise, all technical and scientific terms used herein have the same meaning as commonly understood by one of ordinary skill in the art to which this invention is related. The following terms are defined for purposes of the invention as described herein.

The symbol $\sim\!\!\sim\!\!\sim$, whether utilized as a bond or displayed perpendicular to a bond indicates the point at which the displayed moiety is attached to the remainder of the molecule, solid support, etc.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In some embodiments, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science* 66:1-19 (1997)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science* 66:1-19 (1997)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. The term "prodrug" comprises derivatives of active drugs which have been modified by the addition of a chemical group. This chemical group usually reduces or eliminates the drug's biological activity while, at the same time, conferring some other property to the drug. Once the chemical group has been cleaved from the prodrug, by hydrolysis, reduction, oxidation, light, heat, cavitation, pressure, and/or enzymes in the surrounding environment, the active drug is generated. Prodrugs may be designed as reversible drug derivatives and utilized as modifiers to enhance drug transport to site-specific tissues. Prodrugs are described in the art, for example, in R. L. Juliano (ed.), *Biological Approaches to the Controlled Delivery of Drugs*, Annals of the New York Academy of Sciences, Vol 507 (1998); Hans Bundgaard (ed.), *Design of Prodrugs*, Elsevier Science, (1986); and Kenneth Sloan (ed.), *Prodrugs: Topical and Ocular Delivery*, Drugs and the Pharmaceutical Sciences, Vol 53 (1992).

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "alkyl," by itself or as part of another substituent means, unless otherwise stated, a straight or branched chain, or cyclic hydrocarbon radical, or combination thereof, which may be fully saturated, mono- or polyunsaturated multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkylene," as used herein, is a divalent radical derived from an alkyl.

In some embodiments, alkyl groups of use in the present invention contain between about one and about twenty five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of at least one hydrocarbon and at least one heteroatom which is selected from the group consisting of O, N, Si, P and S, and wherein the nitrogen, phosphorous and sulfur atoms are optionally oxidized, and the nitrogen heteroatom is optionally be quaternized. The heteroatom(s) O, N, P, S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 3 rings), which are fused together or linked covalently. The term "heteroaryl" refers to aryl groups (or rings) that contain from one to four heteroatoms which are a member selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

Each of the above terms (e.g., "alkyl," "heteroalkyl," "aryl" and "heteroaryl") includes both substituted and unsubstituted forms of the indicated radical. Some substituents for each type of radical are provided below.

Substituents for alkyl, heteroalkyl, alkylene, alkenyl, heteroalkylene, heteroalkenyl, alkynyl, cycloalkyl, heterocycloalkyl, cycloalkenyl, and heterocycloalkenyl can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R" R"', —OC(O)R', —C(O)R', —CO$_2$R', —CONR'R", —OC(O)NR'R", —NR"C(O)R', —NR'—C(O)N"', —NR"C(O)$_2$R', —NR—C'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted (C$_1$-C$_6$)alkyl.

As used herein, the term "heteroatom" includes oxygen (O), nitrogen (N), sulfur (S), phosphorus (P) and silicon (Si).

A "substituent group," as used herein, means a group selected from the following moieties:

(A) —OH, —NH$_2$, —SH, —CN, —CF$_3$, oxy, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:
  (i) oxy, —OH, —NH$_2$, —SH, —CN, —CF$_3$, halogen, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxy, —OH, —NH$_2$, —SH, —CN, —CF$_3$, halogen, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from oxy, —OH, —NH$_2$, —SH, —CN, —CF$_3$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2- to 20-membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "amino" or "amine group" refers to the group —NR'R" (or N$^+$RR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N+RR'R" and its biologically compatible anionic counterions.

The term "aqueous solution" as used herein refers to a solution that is predominantly water and retains the solution characteristics of water. Where the aqueous solution contains solvents in addition to water, water is typically the predominant solvent.

The term "linker" or "L" as used herein refers to a single covalent bond or a series of stable covalent bonds incorporating 1-20 nonhydrogen atoms selected from the group consisting of C, N, O, S and P that covalently attach the present quenching compounds to another moiety such as a chemically reactive group or a conjugated substance including biological and non-biological substances. A "cleavable linker" is a linker that has one or more covalent bonds that may be broken by the result of a reaction or condition. For example, an ester in a molecule is a linker that may be cleaved by a reagent, e.g. sodium hydroxide, resulting in a carboxylate-containing fragment and a hydroxyl-containing product.

The terms "protein" and "polypeptide" are used herein in a generic sense to include polymers of amino acid residues of any length. The term "peptide" is used herein to refer to polypeptides having less than 250 amino acid residues, typically less than 100 amino acid residues. The terms apply to amino acid polymers in which one or more amino acid residues are an artificial chemical analogue of a corresponding naturally occurring amino acid, as well as to naturally occurring amino acid polymers.

The term "rt", as used herein, refers to room temperature.

"MCHC," is the mean corpuscular hemoglobin concentration.

"SAD-1" is a transgenic mouse model of sickle cell disease as described by Trudel et. al., *EMBO J,* 10 (11): 3157-3165 (1991).

The term "substituted or unsubstituted ring," as used herein refers to substituted or unsubstituted cycloalkyl, substituted or unsubstituted heterocycloalkyl, substituted or unsubstituted heteroaryl, and substituted or unsubstituted aryl.

"Imine", as used herein, refers to a compound with the following structure:

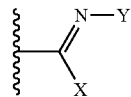

wherein Y and X have the same definitions as set forth in Formula (I), above.

The term "glaucoma" refers to an optic neuropathy or degenerative state usually associated with elevation of intraocular pressure. See, Shields, TEXTBOOK OF GLAUCOMA (4$^{th}$ Ed.), 1997, Lippincott, Williams and Wilkins, which is incorporated herein by reference. The mechanism by which elevated eye pressure injures the optic nerve is not well understood. It is known that axons entering the inferotemporal and superotemporal aspects of the optic disc are damaged. As fibers of the disc are destroyed, the neural rim of the optic disc shrinks and the physiologic cup within the optic disc enlarges. A term known as pathologic "cupping" refers to this shrinking and enlarging process. Although it is possible to measure the cup-to-disc ratio, it is not a useful diagnostic tool because it varies widely in the population. However, it can be used to measure the progression of the disease in an individual by a series of measurements in a time period.

Glaucoma is not a single disease but a group of conditions with various causes. In most cases, these conditions produce increased pressure within the eye. Ultimately glaucoma can lead to optic nerve damage and the loss of visual function. It is not unusual for persons who exhibit gradual development of intraocular pressure to exhibit no symptoms until the end-stage of the disease is reached.

The term "open angle glaucoma"—refers to a chronic type of glaucoma. Occurring in approximately 1% of Americans, open-angle glaucoma is the most common type of glaucoma. Open-angle glaucoma is characterized by a very gradual, painless rise of pressure within the eye. Subjects with open-angle glaucoma exhibit no outward manifestations of disease until irreversible vision impairment.

"Normal tension glaucoma" commonly referred to as low tension glaucoma is a form of open angle glaucoma that accounts for about ⅓ of open-angle glaucoma cases in the United States.

"Angle closure glaucoma" is a glaucoma most prevalent in people who are far-sighted. In angle closure glaucoma, the anterior chamber of the eye is smaller than average hampering the ability of the aqueous humor to pass between the iris and the lens on its way to the anterior chamber, causing fluid pressure to build up between the iris.

"Acute glaucoma" is caused by a sudden increase in intraocular pressure. This intense rise in pressure is accompanied by severe pain. In acute glaucoma, there are outward manifestations of the disease including red eye, cornea swelling and clouding over.

The term "pigmentary glaucoma" refers to a hereditary condition which develops more frequently in men than in woman and begins in the twenties or thirties. pigmentary glaucoma affects persons of near-sightedness. Myopic eyes have a concave-shaped iris creating an unusually wide angle. The wideness of the angle causes the pigment layer of the eye to rub on the lens when the pupil constricts and dilates during normal focusing. The rubbing action ruptures the cells of the iris pigment epithelium, thereby releasing pigment particles into the aqueous humor and trabecular meshwork. If pigment plugs the pores of the trabecular meshwork, drainage is inhibited.

The term "exfoliation syndrome" refers to a type of glaucoma most common in persons of European descent. Exfoliation syndrome is characterized by a whitish material that builds on the lens of the eye. Movement of the iris causes this material to be rubbed off the lens along with some pigment from the iris. Both the pigment and the whitish exfoliation material clog the meshwork, inhibiting drainage of the aqueous humor.

The term "trauma related glaucoma" refers to a type of glaucoma caused by an external force acting upon the eye, i.e., chemical burn, blow to the eye. Trauma related glaucoma occurs when this external force causes a mechanical disruption or physical change with in the eye's drainage system.

"Congenital glaucoma" occurs in about 1 in 10,000 births. It may appear up until age 4. Primary congenital glaucoma is due to abnormal development of the trabecular meshwork. Congenital glaucoma can be hereditary as well as non-hereditary. In congenital glaucoma, the eye enlarges or the cornea becomes hazy. The stretching of the cornea causes breaks to occur in the inner lining. The breaks allow aqueous humor to enter the cornea causing it to swell. As the cornea continues to stretch, more aqueous humor is let in and there is an increase in edema and haze in the cornea.

The term "Sturge-Weber Syndrome" refers to a rare syndrome characterized by a facial birthmark which is port wine in color. The birthmark is associated with an abnormal blood vessels on the surface of the brain. These vascular malformations may affect the eyelids, sclera, conjunctiva, and iris. One third of patients with Sturge-Weber syndrome suffer from increased intraocular pressure. This increased pressure leads to glaucoma. A vascular malformation of the sclera causes elevated pressure in the veins. This elevated pressure in the veins drains the eye thereby causing the intraocular pressure to rise and resulting in damage to the drainage system of the eye.

The term "uveitis" refers to a disease characterized by inflammation of the choroid, ciliary body and iris. In anterior uveitis, a decrease in aqueous humor formation may cause dangerously low levels of pressure within the eye. In other forms of uveitis, i.e., posterior uveitis, the intraocular pressure is elevated. The elevation may be caused by active inflammation, insufficient antiinflammatory therapy, excessive corticosteroid use or insufficient glaucoma therapy. If the inflammation is chronic and not properly controlled, it can lead to trabecular cell death.

The term "chronic elevation" refers to increased pressure caused by a condition that is reoccurring and not treatable.

The term "acute elevation" refers to a sudden increase in intraocular eye pressure. The sudden rise can occur within hours and causes pain within the eye and may even cause nausea and vomiting The term "gradual elevation" refers to a slow increase of pressure within the eye. There are no symptoms associated with the increased rise.

An "ophthalmically acceptable carrier" is a carrier that has substantially no long term or permanent detrimental effect on the eye to which it is administered.

A "bicyclic fused ring" is a cycloalkyl, heterocycloalkyl, aryl, or heteroaryl ring that shares at least 2 vertices with another cycloalkyl, heterocycloalkyl, aryl, or heteroaryl ring parent compound. A tricyclic fused ring is a cycloalkyl, heterocycloalkyl, aryl, or heteroaryl ring that shares at least 2 vertices with another cycloalkyl, heterocycloalkyl, aryl, or heteroaryl ring parent compound.

The term "sickle cell disease" means a red blood cell disorder characterized by the presence of one or more mutated hemoglobin genes. Exemplary mutated hemoglobin genes include, for example, $\beta^{6Glu \rightarrow Val}$ (Hemoglobin S), $\beta^{6Glu \rightarrow Lys}$ (Hemoglobin C), $\beta 2^{6Glu \rightarrow Val}$ (Hemoglobin E), $\beta^{98Val \rightarrow Met}$ (Hemoglobin Köln), $\beta^{99Asp \rightarrow His}$ (Hemoglobin Yakima), $\beta^{102Asn \rightarrow Lys}$ (Hemoglobin Kansas), or combinations thereof. Sickle cell diseases include, for example, sickle cell trait (the heterozygous state of hemoglobin S), sickle cell anemia (the homozygous state of hemoglobin S), hemoglobin SC disease (hemoglobin S present with hemoglobin C), hemoglobin SD disease (hemoglobin S present with hemoglobin D), S/$\beta^{\circ}$ thalassemia (hemoglobin S with a $\beta^{\circ}$ thalassemia mutation), and S/$\beta^{+}$ thalassemia (hemoglobin S with a $\beta^{+}$ thalassemia mutation). Current treatments for sickle cell diseases include, for example, administration of compounds such as antisickling agents (e.g. hydroxyurea), erythropoietin, and/or antibiotics (e.g. ceftriaxone and erythromycin), and allogenic bone marrow transplantation.

Samples or assays comprising IK1 channels that are treated with a potential activator, inhibitor, or modulator are compared to control samples without the inhibitor, activator, or modulator to examine the extent of inhibition or activation. Control samples (untreated with inhibitors) are assigned a relative protein activity value of 100%. Inhibition is achieved when the activity value relative to the control is about 90%, preferably 50%, more preferably 25-0%. Activation is achieved when the activity value relative to the control (untreated with activators) is 110%, more preferably 150%, more preferably 200-500% (i.e., two to five fold higher relative to the control), more preferably 1000-3000% higher. The activity value can be activity of the IK1 channel, e.g., decreased or increased ion flow, or a related phenotype, such as decreasing intraocular pressure, reducing erythrocyte dehydration, or inhibiting normal or abnormal cellular proliferation.

The IK1 channel is a calcium activated channel, also called SK4, KCa4, IKCa, SMIK, and Gardos. The term "IK1" as used herein, refers to both native and cloned intermediate conductance, calcium activated potassium channels. Intermediate conductance, calcium activated potassium channels have been previously described in the literature by their electrophysiology. For example, the Gardos channel, a well known IK channel, is opened by submicromolar concentrations of internal calcium and has a rectifying unit conductance, ranging from 50 pS at −120 mV to 13 pS at 120 mV (symmetrical 120 mM K+; Christopherson, *J. Membrane Biol.* 119, 75-83 (1991)). IK1 channels are blocked by charybdotoxin (CTX) but not the structurally related peptide iberiotoxin (IBX), both of which block BK channels (Brugnara et al., *J. Membr. Biol.* 147:71-82 (1995)). IK1 channels are also blocked by maurotoxin. Apamin, a potent blocker of certain native (Vincent et al., *J. Biochem.* 14:2521 (1975); Blatz & Magleby, *Nature* 323:718-720 (1986)) and cloned SK channels does not block IK1 channels (de-Allie et al., *Br. J. Pharm.* 117:479-487 (1996)). The Gardos channel is also blocked by some imidazole compounds, such as clotrimazole, but not ketoconazole (Brugnara et al, 1993, *J. Clin. Invest.*, 92, 520-526). IK1 channels can therefore be distinguished from the other calcium activated potassium channels by their biophysical and pharmacological profiles. IK1 channels from different tissues have been reported to possess a wide range of unit conductance values.

Human IK1 channels have been cloned and characterized (see, e.g., Ishii et al., *Proc. Nat'l Acad. Sci. USA* 94:11651-11656 (1997); Genbank Accession No. AF0225150; Joiner et al., *Proc. Nat'l Acad. Sci. USA* 94:11013-11018 (1997); Genbank Accession No. AF000972; Lodsdon et al., *J. Biol. Chem.* 272:32723-32726 (1997); Genbank Accession No. AF022797; and Jensen et al., *Am. J. Physiol.* 275:C848-856 (1998); see also WO 98/11139; WO 99/03882; WO 99/25347; and WO 00/12711). Non-human IK1 channels have also been cloned, e.g., from mouse and rat (see, e.g., Vandorpe et al., *J. Biol. Chem.* 273:21542-21553 (1998); Genbank Accession No. NM_032397; Warth et al., *Pflugers Arch.* 438:437-444 (1999); Genbank Accession No. AJ133438; and Neylon et al., *Circ. Res.* (online)85:E33-E43 (1999); Genbank Accession No. AF190458). The gene for the IK1 channel is named KCNN4 and it is located on chromosome 19q13.2 (Ghanshani et al., *Genomics* 51:160-161 (1998)).

III. The Compounds

III. a) Compound Description

The compounds which are capable of reducing or inhibiting ion flow through the Gardos channel and/or reducing or inhibiting mammalian cell proliferation according to the invention are generally tri-(aryl or heteroaryl) methane compounds or analogues thereof which further comprise an imine moiety. Thus, in a first aspect, the present invention provides a compound having a structure according to Formula (I):

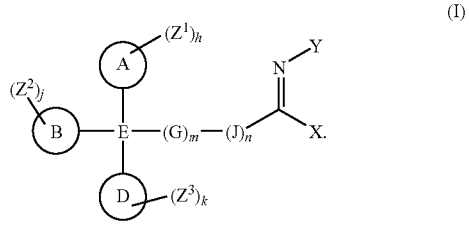

In some embodiments, the compound exists as a pharmaceutically acceptable salt or prodrug.

The rings A, B, and D are independently selected from substituted or unsubstituted aryl, and substituted or unsubstituted heteroaryl. E is C, P, Si, or Ge. G is substituted or unsubstituted alkylene, or substituted or unsubstituted heteroalkylene. J is $-N(R^1)-$, $-O-$, or $-S-$.

X is H, substituted or unsubstituted alkyl, $-NR^2R^3$, $-R^{4a}$, or $-OR^{5a}$. Y is $-R^6$, $-OR^7$, or $-NR^8R^9$.

The ring substituents $Z^1$, $Z^2$, and $Z^3$ are independently H, hydroxyl, amino, cyano, nitro, halogen, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, $-SR^{4b}$, $-OR^{5b}$, $-P(O)R^{10a}R^{11a}$, $-S(O)_{q1}R^{12a}R^{13a}$, $-S(O)_{q1}R^{12a}$, $-NR^{14}R^{15}$, $-N(R^{14})C(O)R^{15}$, $-C(O)R^{15}$, $-C(O)NR^{14}R^{15}$, or $-PR^{14}R^{15}$. The symbol q1 represents the integers 1 or 2.

The symbols h, j, and k are integers independently selected from 0, 1, 2, 3, 4, and 5. In some embodiments, at least one of h, j, or k is not 0. In other embodiments, at least two of h, j, or k is not 0. In some embodiments, the symbols h, j, and k are integers independently selected from 1, 2, 3, 4, and 5. The symbols m and n are integers independently selected from 0 and 1.

$R^1$ is selected from H, amino, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, $-P(O)R^{10b}R^{11b}$, $S(O)_{q2}R^{12b}R^{13b}$, $-S(O)_{q2}R^{12b}$ and $-C(O)R^{17a}$. The symbol q2 is an integer selected from 1 and 2.

$R^2$ is selected from H, hydroxyl, amino, substituted or unsubstituted alkyl, substituted or unsubstituted cycloalkyl, substituted or unsubstituted heteroalkyl, substituted or unsubstituted heterocycloalkyl, substituted or unsubstituted aryl, and substituted or unsubstituted heteroaryl. $R^3$ is selected from H, hydroxyl, amino, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, $-P(O)R^{10c}R^{11c}$, $-S(O)_{q3}R^{12c}$, $-S(O)_{q3}R^{12c}R^{13c}$, or $-C(O)R^{17b}$. The symbol q3 is an integer selected from 1 and 2. $R^2$ and $R^3$ are optionally joined to form a substituted or unsubstituted heterocycloalkyl or substituted or unsubstituted heteroaryl with the nitrogen to which they are attached.

$R^{4a, b}$ (i.e. $R^{4a}$ and $R^{4b}$) are independently selected from H, substituted or unsubstituted alkyl, substituted or unsubstituted cycloalkyl, substituted or unsubstituted heteroalkyl, substituted or unsubstituted heterocycloalkyl, substituted or unsubstituted aryl, and substituted or unsubstituted heteroaryl. $R^{5a,b}$ are independently selected from H, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, $-P(O)R^{10d}R^{11d}$, $-S(O)_{q4}R^{12d}$, and $-S(O)_{q4}R^{12d}R^{13d}$. The symbol q4 is an integer selected from 1 and 2.

$R^6$ is selected from H, cyano, $-NO_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $-P(O) R^{10e}R^{11e}$, $-S(O)_{q5}R^{12e}$, and $-S(O)_{q5}R^{12e}R^{13e}$. The symbol q5 is an integer selected from 1 and 2.

$R^7$ is selected from H, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, —C(O)R$^{10e}$, and —P(O)R$^{10f}$R$^{11f}$. R$^8$ is selected from H, substituted or unsubstituted alkyl, substituted or unsubstituted cycloalkyl, substituted or unsubstituted heteroalkyl, and substituted or unsubstituted heterocycloalkyl, substituted or unsubstituted aryl, and substituted or unsubstituted heteroaryl. R$^9$ is H, —OH, CN, nitro, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, —P(O)R$^{10g}$R$^{11g}$, —S(O)$_{q6}$R$^{12f}$, —S(O)$_{q6}$R$^{12f}$R$^{13f}$, or —C(O)R$^{17c}$. The symbol q6 is an integer selected from 1 and 2. R$^8$ and R$^9$ are optionally joined to from a substituted or unsubstituted heterocycloalkyl or substituted or unsubstituted heteroaryl with the nitrogen to which they are attached.

R$^{10a, b, c, d, e, f}$ and R$^{11a, b, c, d, e, f}$ are independently selected from, amino, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, and —OR$^{16}$. R$^{16}$ is independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, R$^{16}$ is independently hydrogen or substituted or unsubstituted $C_1$-$C_{10}$ alkyl. For each R$^{10}$/R$^{11}$ pair, only one of R$^{10}$ and R$^{11}$ may be amino. Thus, R$^{10a}$ and R$^{11a}$, R$^{10b}$ and R$^{11a}$ and R$^{10c}$, R$^{11c}$ and R$^{10d}$ and R$^{11d}$, R$^{10e}$ and R$^{11e}$, R$^{10f}$ and R$^{11f, and R10g}$ and R$^{11g}$ are not simultaneously amino.

R$^{12a, b, c, d, e, f, g}$ and R$^{13a, b, c, d, e, f, g}$ are independently selected from amino, substituted or unsubstituted alkyl, substituted or unsubstituted cycloalkyl, substituted or unsubstituted heteroalkyl, substituted or unsubstituted heterocycloalkyl, substituted or unsubstituted aryl, and substituted or unsubstituted heteroaryl.

R$^{14}$ and R$^{15}$ are independently selected from substituted or unsubstituted alkyl, substituted or unsubstituted cycloalkyl, substituted or unsubstituted heteroalkyl, substituted or unsubstituted heterocycloalkyl, substituted or unsubstituted aryl, and substituted or unsubstituted heteroaryl.

R$^{17a, b, c}$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, and —OR$^{18}$. R$^{18}$ is independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

Y and X, together with the atoms to which they are attached, are optionally joined to form a substituted or unsubstituted membered ring (e.g. a 5- to 7-membered ring). Z$^1$ and X, together with the atoms to which they are attached, are optionally joined to form a bicyclic fused ring. Z$^3$ and X, together with the atoms to which they are attached, are optionally joined to form a bicyclic fused ring. Z$^1$ and Z$^2$, together with the atoms to which they are attached, are optionally joined to form a tricyclic fused ring. Z$^1$ and Z$^3$, together with the atoms to which they are attached, are optionally joined to form a tricyclic fused ring. Z$^2$ and Z$^3$, together with the atoms to which they are attached, are optionally joined to form a tricyclic fused ring.

In some embodiments, E is C. In some related embodiments, A, B, and D are selected from substituted or unsubstituted phenyl, and substituted or unsubstituted pyridinyl. In other related embodiments A, B, and D are phenyl. In other related embodiments, m and n are 0.

In some embodiments, X is hydrogen, —NH$_2$, —N(H)C(NH)NH$_2$, or substituted or unsubstituted $C_1$-$C_{10}$ alkyl.

In other embodiments, A, B, and D are independently selected from substituted or unsubstituted phenyl, substituted or unsubstituted pyridinyl, substituted or unsubstituted pyrazinyl, substituted or unsubstituted pyrimidinyl, substituted or unsubstituted imidazolyl, substituted or unsubstituted thiazolyl, substituted or unsubstituted oxazolyl, substituted or unsubstituted furanyl, substituted or unsubstituted pyrrolyl, and substituted or unsubstituted thiophenyl. A, B, and D may also be independently selected from substituted or unsubstituted phenyl and substituted or unsubstituted pyridinyl.

Z$^1$, Z$^2$, and Z$^3$ may be independently selected from H, hydroxyl, halogen, substituted or unsubstituted alkyl, substituted or unsubstituted heteroalkyl, —P(O)R$^{10a}$R$^{11a}$, and —S(O)R$^{12a}$. The symbols m and n may be simultaneously 0.

R$^{10a, b, c, d, e, f, g}$ and R$^{11a, b, c, d, e, f, g}$ may be indepently selected from H, —OH, —OCH$_3$, and —ONH$_4$. R$^{12a, b, c, d, e, f}$ and R$^{13a, b, c, d, e, f}$ may be independently selected from H, =O, —OH, and —CH$_3$.

In some embodiments, Y is —R$^6$, where R$^6$ is H, CN, or —S(O)$_{q5}$R$^{12e}$. In some related embodiments, q5 is 2, and R$^{12e}$ is substituted or unsubstituted $C_1$-$C_{10}$ alkyl.

In other embodiments, Y is —OR$^7$. In some related embodiments, R$^7$ is H, substituted or unsubstituted $C_1$-$C_{10}$alkyl, —C(O)R$^{10f}$, or —P(O)R$^{10f}$R$^{11f}$. In some embodiments, where R$^7$ is —C(O)R$^{10f}$, R$^{10f}$ is substituted or unsubstituted $C_1$-$C_{10}$ alkyl (e.g. a $C_1$-$C_{10}$ alkyl substituted with —NH$_2$). In some embodiments, where R$^7$ is —P(O)R$^{10f}$R$^{11f}$, R$^{10f}$ and R$^{11f}$ are independently —OR$^{16}$, where R$^{16}$ may be H or substituted or unsubstituted $C_1$-$C_{10}$ alkyl.

In other embodiments, Y is —NR$^8$R$^9$. In some related embodiments, R$^8$ is hydrogen. In other related embodiments, R$^9$ is —P(O)R$^{10g}$R$^{11g}$, —S(O)$_{q6}$R$^{12f}$, or —C(O)R$^{17c}$. In some embodiments, where R$^9$ is —P(O)R$^{10g}$R$^{11g}$, R$^{10g}$ and R$^{11g}$ are independently —OR$^{16}$ where R$^{16}$ is independently hydrogen or substituted or unsubstituted $C_1$-$C_{10}$ alkyl. In some embodiments, where R$^9$ is —S(O)$_{q6}$R$^{12f}$, R$^{12f}$ is substituted or unsubstituted $C_1$-$C_{10}$ alkyl, and q6 is 2. In some embodiments, where R$^9$ is —C(O)R$^{17c}$C, R$^{17c}$ is substituted or unsubstituted $C_1$-$C_{10}$ alkyl (e.g. a $C_1$-$C_{10}$ alkyl substituted with —NH$_2$).

In still other embodiments of the current invention, the compound is a selected from those listed in Table 1 below. The compound may also be selected from those listed in Table 2 below.

In another aspect, the present invention provides a compound having a structure according to Formula (II):

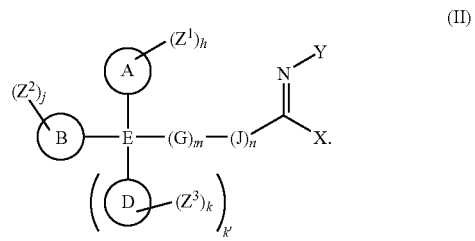

(II)

In Formula (II), $Z^1$, $Z^2$, $Z^3$, h, j, k, A, B, D, G, J, m, n, Y, and X are as defined above in the discussion of Formula (I).

E is selected from C, P, Si, Ge, $N^+$, and N. The symbol k' represents an integer selected from 0 and 1. Where E is C, P, Si, Ge, or $N^+$, k' is 1. Where E is N, k' is 0. One of skill in that art will recognize that any appropriate counter ion (e.g. a negatively charged compound of element) may be present where E is $N^+$. Useful counter ions may include, for example, sulfate, acetate, bicarbonate, carbonate, citrate, fluoride, iodide, lauryl sulfate, molybdate, oxalate, perchlorate, persulfate, sulfate, sulfide, thiosulfate, vanadate, and the like.

In some embodiments, each substituted group described above in the compound of Formulae (I), and/or (II) is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, and/or substituted heteroalkylene, described above in the compounds of Formulae (I) and/or (II) is substituted with at least one substituent group. In other embodiments, at least one or all of these groups are substituted with at least one size-limited substituent group. Alternatively, at least one or all of these groups are substituted with at least one lower substituent group.

In other embodiments of the compounds of Formulae (I) and/or (II), each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, each substituted or unsubstituted heterocycloalkyl is a substituted or unsubstituted 4 to 8 membered heterocycloalkyl, each substituted or unsubstituted alkylene is a substituted or unsubstituted $C_1$-$C_{20}$ alkylene, and/or each substituted or unsubstituted heteroalkylene is a substituted or unsubstituted 2 to 20 membered heteroalkylene.

Alternatively, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, each substituted or unsubstituted heterocycloalkyl is a substituted or unsubstituted 5 to 7 membered heterocycloalkyl, each substituted or unsubstituted alkylene is a substituted or unsubstituted $C_1$-$C_8$ alkylene, and/or each substituted or unsubstituted heteroalkylene is a substituted or unsubstituted 2 to 8 membered heteroalkylene.

III b) Compound Preparation

The following exemplary schemes illustrate methods of preparing the compounds of the invention. These methods are not limited to producing the compounds listed, but can be used to prepare other substrates as well. The compounds of the invention can also be produced by methods not explicitly illustrated in the schemes. The compounds can be prepared using readily available starting materials or known intermediates.

The invention provides three methods of synthesizing the tri-(aryl or heteroaryl) nitrile intermediates of the invention. Two of the methods are outlined in Schemes 1-3. The third method is outlined in Schemes 4-5.

The tri-(aryl or heteroaryl) substituents of the invention can be produced through the methods outlined in Scheme 1 or Scheme 2. For the purposes of illustration, three phenyl rings represent the tri-(aryl or heteroaryl) rings.

In the schemes below, $Z^1$, $Z^2$, $Z^3$, X, and Y are as defined above in Formula (I) unless otherwise noted.

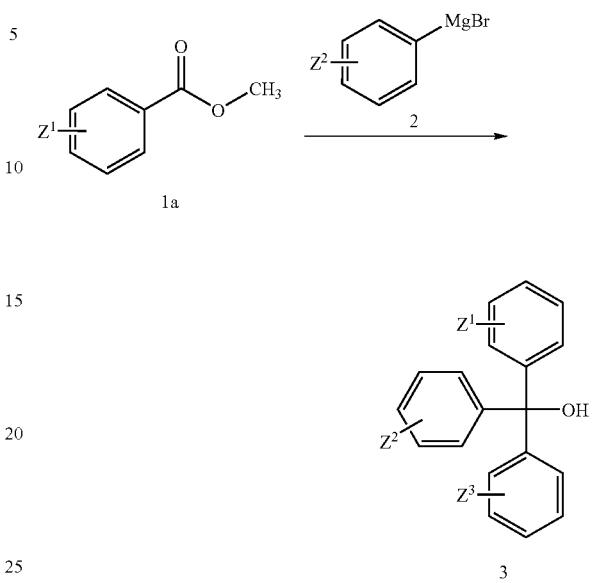

In Scheme 1, a substituted or unsubstituted phenyl acetyl ester 1a is reacted with a Grignard reagent comprising a phenyl ring 2 in order to produce 3. Note that two molecules of the Grignard reagent add to 1a in order to produce 3. Thus, in Scheme 1, $Z^2$ is equal to $Z^3$.

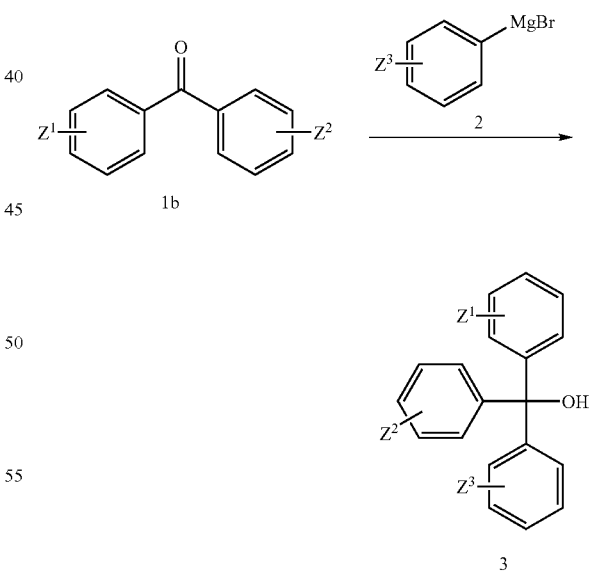

In Scheme 2, a substituted or unsubstituted benzophenone 1b is reacted with a Grignard reagent comprising a phenyl ring 2 in order to produce 3.

In Scheme 3, t e alcohol moiety on the compound is converted into a nitrile.

Scheme 3

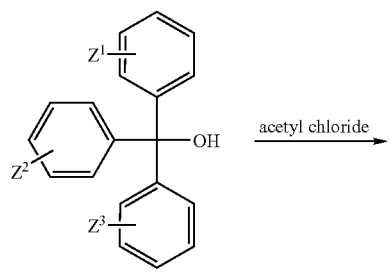

In Scheme 3, 3 is reacted with acetyl chloride to generate 13, and 13 was converted to 4 with copper cyanide.

The third alternative for producing the tri-(aryl or heteroaryl) nitrile intermediates of the invention is outlined in Schemes 4-5 below. For the purposes of illustration, three pyridine rings represent the tri-(aryl or heteroaryl) rings.

Scheme 4

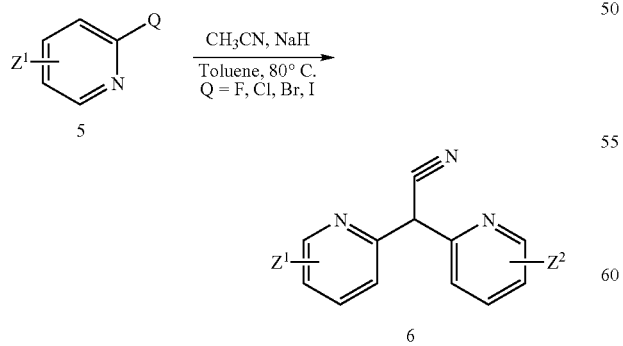

In Scheme 4, 5 is reacted with a second molecule of 5 (with the same or different Z substituent), as well as acetonitrile and sodium hydride, in toluene, to yield 6.

Scheme 5

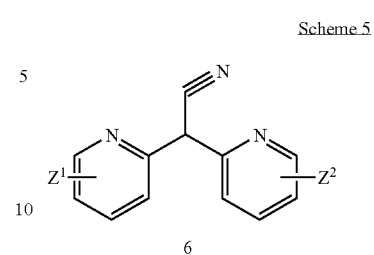
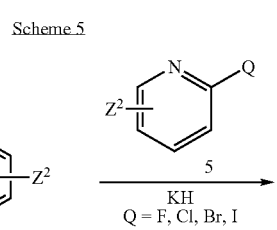

A third molecule of 5 (with the same or different Z substituent) is then reacted with 6 and potassium hydride in order to afford 7.

Once the nitrile compound is produced, the molecule can undergo a series of reactions to form the imine or substituted imine compounds of the invention.

Schemes 6-8 illustrate these reactions.

Scheme 6

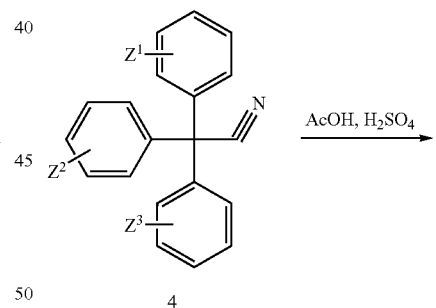
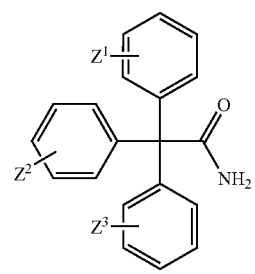

In Scheme 6, 4 is reacted with acetic acid in sulfuric acid to convert the nitrile functional group into an amide group in 8. Note that 7 could be used in place of 4 in this Scheme.

Scheme 7

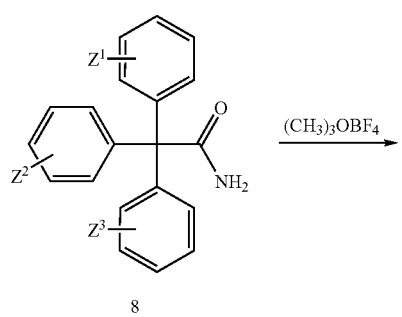

8

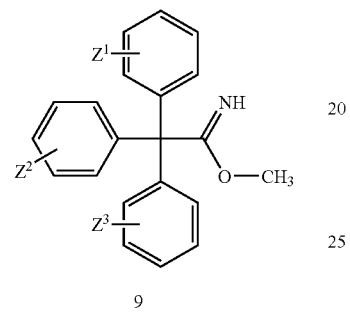

9

In Scheme 7, 8 is reacted with a borofluoride in order to produce 9.

Scheme 8

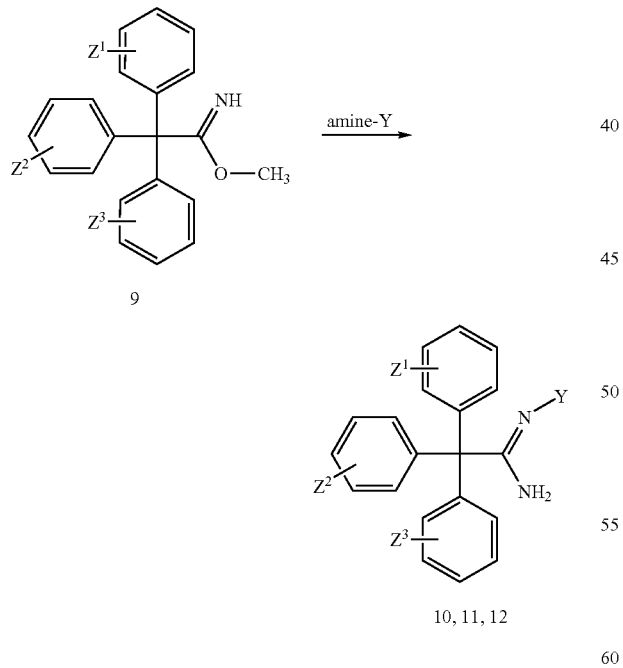

In Scheme 8, 9 is reacted with a substituted or unsubstituted amine in order to produce 10, 11, and 12.

Another strategy for preparing the compounds of the invention is shown in Schemes 9-12. For the purposes of illustration, three phenyl rings represent the tri-(aryl or heteroaryl) rings.

Scheme 9

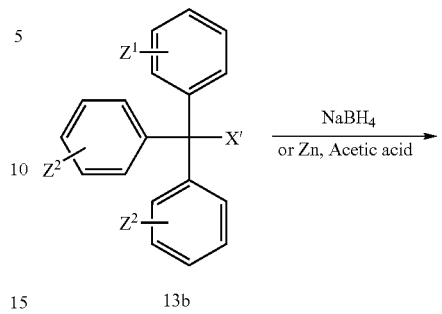

13b

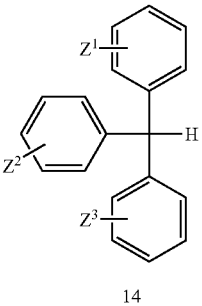

14

In Scheme 9, 13 is reduced by either sodium borohydride or zinc and acetic acid in order to yield 14 using the method outline in Maltese et al., *Journal of Organic Chemistry* 66(23), 7615-7625 (2001). The symbol X' is Cl or Br.

Scheme 10

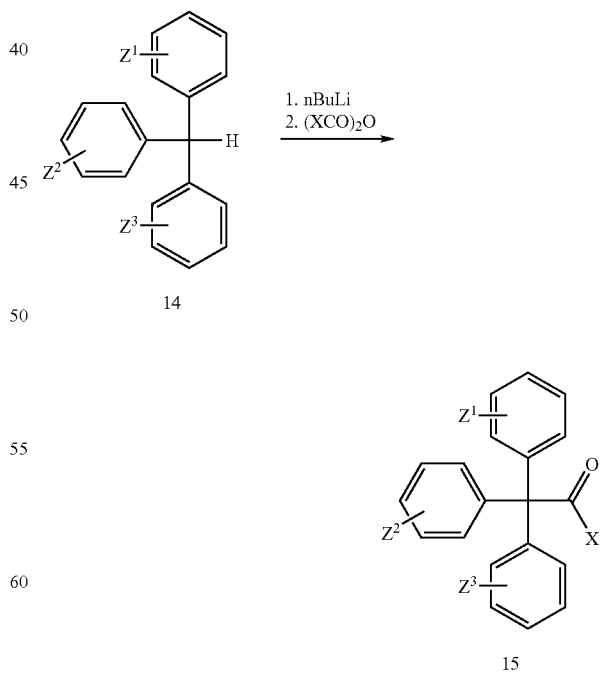

In Scheme 10, 14 is reacted first with n-butyl lithium, and then a substituted acetic anhydride in order to produce 15.

Scheme 11

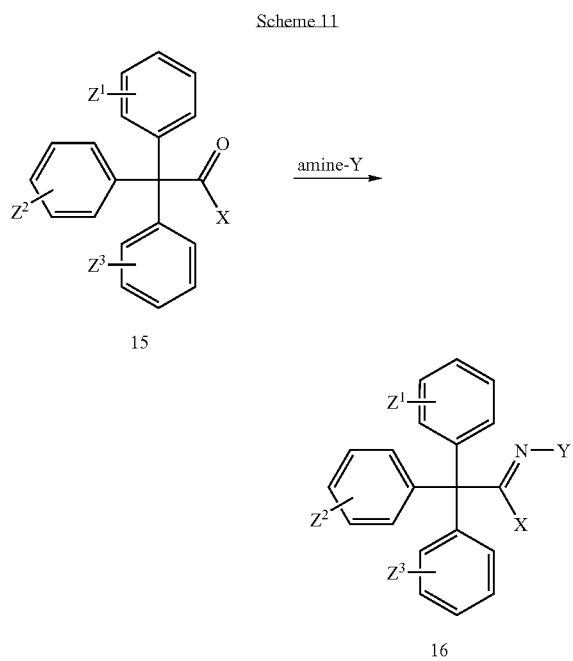

In Scheme 11, 15 is reacted with a substituted or unsubstituted amine in order to produce 16.

IV. Determining the Effectiveness of the Compounds

IV. a) Testing Compound Stability

For compounds to act as pharmaceutically useful Gardos channel inhibitors, candidate compounds must demonstrate both acceptable bioavailability and stability in vivo. Stability is particularly important for treating a chronic syndrome such as sickle cell anemia. Subjects undergoing treatment for sickle cell anemia must be regularly dosed with the anti-sickling agent (e.g., the Gardos channel inhibitor) throughout the duration of their life. Among other concerns, such a life-long dosage regimen presents a serious risk of variable patient compliance with the regimen. If the titer of the medication in the patient's system decreases as a result of poor compliance, this raises the risk of the occurrence of a sickle cell event and the concomitant pain and physical and physiological damage. Compounds having increased in vivo residence times and increased bioavailability allow for a simplified dosage regimen (i.e. fewer doses/day and/or less medication). Moreover, reducing the amount of compound administered carries with it the promise of reducing side effects resulting from the medication and/or its metabolites. Thus, it is highly desirable to provide Gardos channel inhibitors demonstrating good bioavailabilities and enhanced in vivo stabilities.

IV. b) Testing Compound Activity

To develop pharmaceutically useful Gardos channel inhibitors, candidate compounds must demonstrate acceptable activity towards the target channel. Compounds are judged to be sufficiently potent if they have an $IC_{50}$ towards the Gardos channel of less than 1 µM.

As discussed above in the context of compound stability, this level of activity is particularly important for treating a chronic syndrome such as sickle cell anemia. The various concerns about patient compliance and side effects are well addressed by Gardos channel inhibitors having an $IC_{50}$ towards the Gardos channel of less than 1 µM.

The activity of the compounds of the invention towards ion channels, such as the Gardos channel can be assayed utilizing methods known in the art. For example, see, Brugnara et al., *J. Biol. Chem.*, 268(12): 8760-8768 (1993). Utilizing the methods described in this reference, both the percent inhibition of the Gardos channel and the $IC_{50}$ of the compounds of the invention can be assayed.

In an exemplary assay, the inhibition by test compounds of an erythrocyte Gardos channel can be assayed using human red blood cells. The degree of inhibition can be measured using a detectable material such as $^{86}Rb$. In an exemplary assay, utilizing $^{86}Rb$, Gardos channel inhibition can be assayed by exposing red blood cells to $^{86}Rb$ and a test compound and measuring the amount of $^{86}Rb$ taken up by the cells. Numerous variations on this assay will be apparent to those of skill in the art.

The potency of the compounds of the invention can be assayed using erythrocytes by a method such as that disclosed by Brugnara et al., *J. Clin. Invest.*, 92: 520-526 (1993). Briefly, erythrocytes are exposed to a test compound and a $^{86}Rb$-containing medium. The initial rate of $^{86}Rb$ transport can be calculated from a parameter such as the linear least square slope of $^{86}Rb$ uptake by the cell(s). Inhibitory constants can be calculated by standard methods using computer-assisted nonlinear curve fitting.

Other methods for assaying the activity of ion channels and the activity of agents that affect the ion channels are known in the art. The selection of an appropriate assay methods is well within the capabilities of those of skill in the art. See, for example, Hille, B., *Ionic Channels of Excitable Membranes*, Sinaner Associates, Inc. Sunderland, Mass. (1992).

The results of Gardos channel and erythrocyte inhibition assays utilizing compounds of the invention and other closely-related compounds are displayed in Table 1, below.

IV. c) Testing Compound Selectivity

For compounds to act as pharmaceutically useful Gardos channel inhibitors, candidate compounds must demonstrate acceptable selectivity towards the target channel. Compounds having a selectivity towards the Gardos channel, as measured by the ratio of a compound $IC_{50}$ towards $I_{Ks}$ vs. its $IC_{50}$ towards the Gardos channel of at least 80 are judged to be sufficiently selective. Recordings of $I_{Ks}$ current were made using the whole cell patch clamp methodology on guinea pig myocytes as described in Turgeon et al., *Circulation Research* 75: 879-86 (1994).

The selectivity of a particular compound for the Gardos channel relative to another potassium ion channel is conveniently determined as a ratio of two compound binding-related quantities (e.g., $IC_{50}$). In some embodiments, the selectivity is determined using the activities determined as discussed above, however, other methods for assaying the activity of ion channels and the activity of agents that affect the ion channels are known in the art. The selection of appropriate assay methods is well within the capabilities of those of skill in the art. See, for example, Hille, B., *Ionic Channels of Excitable Membranes*, Sinaner Associates, Inc. Sunderland, Mass. (1992).

As can be seen from the results displayed above, the compounds of the invention demonstrate marked selectivity for the Gardos channel versus other potassium ion channels (e.g., $I_{Ks}$). Moreover, the compounds of the invention are potent inhibitors of the Gardos channel. Additionally, the in vivo half-lives of these compounds are demonstrably enhanced relative to non-fluorinated compounds such as clotrimazole.

In one embodiment, the compounds of the invention are potent, selective and stable inhibitors of potassium flux, such as that mediated by the Gardos channel.

The compound(s) of the invention can be administered per se or in the form of a pharmaceutical composition wherein the active compound(s) is in admixture with one or more pharmaceutically acceptable carriers, excipients or diluents. Thus, in addition to compounds that affect cellular ion fluxes (e.g., Gardos channel inhibiting activity), the present invention also provides pharmaceutical formulations that contain the compounds of the invention.

V. Pharmaceutical Formulations

In a second aspect, the invention provides a pharmaceutical formulation comprising a compound of the invention according to Formulae (I) or (II) admixed with a pharmaceutically acceptable excipient.

The compounds described herein, or pharmaceutically acceptable addition salts or hydrates thereof, can be formulated so as to be delivered to a patient using a wide variety of routes or modes of administration. Suitable routes of administration include, but are not limited to, inhalation, transdermal, oral, ocular, rectal, transmucosal, intestinal and parenteral administration, including intramuscular, subcutaneous and intravenous injections.

The compounds described herein, or pharmaceutically acceptable salts and/or hydrates thereof, may be administered singly, in combination with other compounds of the invention, and/or in cocktails combined with other therapeutic agents. The choice of therapeutic agents that can be co-administered with the compounds of the invention will depend, in part, on the condition being treated.

For example, when administered to patients suffering from sickle cell disease, the compounds of the invention can be administered in cocktails containing agents used to treat the pain, infection and other symptoms and side effects commonly associated with sickle cell disease. Such agents include, e.g., analgesics, antibiotics, etc. The compounds can also be administered in cocktails containing other agents that are commonly used to treat sickle cell disease, including butyrate and butyrate derivatives (Perrine et al., *N. Engl. J. Med.* 328(2): 81-86 (1993)); hydroxyurea (Charache et al., *N. Engl. J. Med.* 323(20): 1317-1322 (1995)); erythropoietin (Goldberg et al, *N. Engl. J. Med.* 323(6): 366-372 (1990)); and dietary salts such as magnesium (De Franceschi et al., *Blood* 88(648a): 2580 (1996)).

Pharmaceutical compositions for use in accordance with the present invention can be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention can be formulated in aqueous solutions, preferably in physiologically compatible buffers such as Hanks's solution, Ringer's solution, or physiological saline buffer. In some embodiments, the formulation comprises water and an alcohol and/or glycol. Other useful components of this formulation include, for example, surfactant, emulsifiers and materials such as ethoxylated oils. An exemplary formulation comprises a compound of the invention, poly(ethyleneglycol) 400, ethanol and water in a 1:1:1 ratio. Another exemplary formulation comprises a compound of the invention, water, poly(ethyleneglycol) 400 and Cremophor-EL.

For transmucosal administration (e.g., buccal, rectal, nasal, ocular, etc.), penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be combined with a solid excipient, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form, such as those described above for intravenous administration. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, when administered to patients suffering from sickle cell disease, the compounds of the invention can be administered in cocktails containing agents used to treat the pain, infection and other symptoms and side effects commonly associated with sickle cell disease. Such agents include, e.g., analgesics, antibiotics, etc. The compounds can also be administered in cocktails containing other agents that are commonly used to treat sickle cell disease, including butyrate and butyrate derivatives (Perrine et al., *N. Engl. J. Med.* 328(2):81-86 (1993)); hydroxyurea (Charache et al., *N. Engl. J. Med.* 323(20):1317-1322 (1995)); erythropoietin (Goldberg et al., *N. Engl. J. Med.* 323(6): 366-372 (1990)); and dietary salts such as magnesium (De Franceschi et al., *Blood* 88(648a):2580 (1996)).

When administered to a patient undergoing cancer treatment, the compounds may be administered in cocktails containing other anti-cancer agents and/or supplementary potentiating agents. The compounds may also be administered in cocktails containing agents that treat the side-effects of radiation therapy, such as anti-emetics, radiation protectants, etc.

Anti-cancer drugs that can be co-administered with the compounds of the invention include, e.g., Aminoglutethimide; Asparaginase; Bleomycin; Busulfan; Carboplatin; Carmustine (BCNU); Chlorambucil; Cisplatin (cis-DDP); Cyclophosphamide; Cytarabine HCl; Dacarbazine; Dactinomycin; Daunorubicin HCl; Doxorubicin HCl; Estramustine phosphate sodium; Etoposide (VP-16); Floxuridine; Fluorouracil (5-FU); Flutamide; Hydroxyurea (hydroxycarbamide); Ifosfamide; Interferon Alfa-2a, Alfa 2b, Lueprolide acetate (LHRH-releasing factor analogue); Lomustine (CCNU); Mechlorethamine HCl (nitrogen mustard); Melphalan; Mercaptopurine; Mesna; Methotrexate (MTX); Mitomycin; Mitotane (o.p'-DDD); Mitoxantrone HCl; Octreotide; Plicamycin; Procarbazine HCl; Streptozocin; Tamoxifen citrate; Thioguanine; Thiotepa; Vinblastine sulfate; Vincristine sulfate; Amsacrine (m-AMSA); Azacitidine; Hexamethylmelamine (HMM); Interleukin 2; Mitoguazone (methyl-GAG; methyl glyoxal bis-guanylhydrazone; MGBG); Pentostatin; Semustine (methyl-CCNU); Teniposide (VM-26); paclitaxel and other taxanes; and Vindesine sulfate.

Supplementary potentiating agents that can be co-administered with the compounds of the invention include, e.g., tricyclic anti-depressant drugs (e.g., imipramine, desipramine, amitriptyline, clomipramine, trimipramine, doxepin, nortriptyline, protriptyline, amoxapine and maprotiline); non-tricyclic and anti-depressant drugs (e.g., sertraline, trazodone and citalopram); $Ca^{2+}$ antagonists (e.g., verapamil, nifedipine, nitrendipine and caroverine); amphotericin (e.g., Tween 80 and perhexiline maleate); triparanol analogues (e.g., tamoxifen); antiarrhythmic drugs (e.g., quinidine); antihypertensive drugs (e.g., reserpine); Thiol depleters (e.g., buthionine and sulfoximine); and calcium leucovorin.

Pharmaceutically acceptable carriers are determined in part by the particular composition being administered, as well as by the particular method used to administer the composition. Accordingly, there are a wide varieties of suitable formulations of pharmaceutical composition. In one embodiment, topical or oral administration and compositions are preferred. In another embodiment, topical administration and compositions are preferred.

Any method of administering drugs directly to a mammalian eye may be employed to administer, in accordance with the present invention, the compound or compounds to the eye to be treated. The primary effect on the mammal resulting from the direct administration of the compound or compounds to the mammal's eye is a reduction in intraocular pressure. More preferably, one or more IK1 blockers and/or additional compounds known to reduce intraocular pressure are applied topically to the eye or are injected directly into the eye. Particularly useful results are obtained when the compound or compounds are applied topically to the eye in an ophthalmic preparation, e.g., as ocular solutions, suspensions, gels or creams, as examples of topical ophthalmic preparations used for dose delivery.

In accordance with the invention the compounds are typically administered in an ophthalmically acceptable carrier in sufficient concentration so as to deliver an effective amount of the compound or compounds to the eye. The compounds are administered in accordance with the present invention to the eye, typically admixed with an ophthalmically acceptable carrier, and optionally with another compound suitable for treatment of glaucoma and/or reduction of intraocular pressure. Any suitable, e.g., conventional, ophthalmically acceptable carrier may be employed including water (distilled or deionized water), saline, and other aqueous media, with or without solubility enhancers such as any of the ophthalmically acceptable beta-cyclodextrins. The compounds may be soluble in the carrier, which is employed for their administration, so that the compounds are administered to the eye in the form of a solution. Alternatively, a suspension of the compound or compounds (or salts thereof) in a suitable carrier may also be employed.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages that are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v. In another embodiment, the dosage range is 10-1000 μg per eye. In another embodiment, the dosage range is 75-150 μg per eye.

When forming compositions for topical administration, the compounds are generally formulated as between about 0.001% to 10% w/v, more preferably between about 0.1% to 5% w/v. In one embodiment, the formulation is 1.0% w/v. In one embodiment, the formulations are solutions in water at a pH preferably between about 5.0 to 8.0 pH, preferably pH 7.4±0.3. In another aspect of the invention, the compounds are formulated as suspensions. In some embodiments, the formulation is in a 1% w/v ophthalmic suspension: 1.0% compound of Formula (I) or (II), micronized; 0.06% carbomer (carbopol 1382), NF; 1.0% poloxamer 188, NF; 2.5% glycerin, USP; 0.01% benzalkonium chloride, NF; sodium hydroxide, NF, q.s. pH 7.4±0.3; and purified water, USP (the formulation may be prepared as % w/w for convenience, and higher grades of water, USP, may be substituted). Other suitable IK1 inhibiting compounds of the invention may be substituted for Formulae (I) or (II) in this formulation. This formulation may contain additional compounds know to reduce intraocular pressure, or may be administered with additional pharmaceutical compositions.

Various preservatives may be used in an ophthalmic preparation. Preservatives include, but are not limited to, benzalkonium chloride, chlorobutanol, thimerosal, phenylmercuric acetate, and phenylmercuric nitrate. Likewise, various vehicles may be used in such ophthalmic preparation. These vehicles include, but are not limited to, polyvinyl alcohol, povidone, cyclodextrines, hydroxypropyl methyl cellulose, poloxamers, carboxymethyl cellulose and hydroxyethyl cellulose. Such preservatives, if utilized, will typically be employed in an amount between about 0.001 and about 1.0% by weight.

Tonicity adjusters may be added as needed or convenient. They include, but are not limited to, salts, particularly sodium chloride, potassium chloride etc., mannitol and glycerin, or any other suitable ophthalmically acceptable tonicity adjuster. Such agents, if utilized, will typically be employed in an amount between about 0.1 and about 1.0% by weight.

Various buffers and means for adjusting pH may be used so long as the resulting preparation is ophthalmically acceptable. Accordingly, buffers include but are not limited to, acetate buffers, titrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to increase ocular absorption of the compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The ophthalmic solution (ocular drops) may be administered to the mammalian eye as often as necessary to maintain an acceptable level of intraocular pressure in the eye. In other words, the ophthalmic solution (or other formulation) is administered to the mammalian eye as often as necessary to maintain the beneficial effect of the active ingredient in the eye. Those skilled in the art will recognize that the frequency of administration depends on the precise nature of the active ingredient and its concentration in the ophthalmic formulation. Within these guidelines it is contemplated that the ophthalmic formulation of the present invention will be administered to the mammalian eye once daily. The formulations may be administered to the mammalian eye anywhere from about 1-4× daily, or as otherwise deemed appropriate by the attending physician. The formulations may also be administered in combination with one or more other pharmaceutical compositions known to reduce intraocular pressure in a subject or otherwise have a beneficial effect in a subject, including miotics (e.g., pilocarpine, carbachol, and acetylcholinesterase inhibitors); sympathomimetics (e.g., epinephrine and dipivalylepinephrine); beta-blockers (e.g., betaxolol, levobunolol and timolol); alpha-2 agonists (e.g., para-amino clonidine); carbonic anhydrase inhibitors (e.g., acetazolamide, methazolamide and ethoxzolamide); and prostaglandins and their analogs and derivatives (e.g., latanaprost).

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403, 841; 5,212,162; and 4,861,760. The entire contents of these patents are incorporated herein by reference.

In addition to the above-described principal ingredients, one skilled in formulating ophthalmic compositions will appreciate that ocular compositions may further comprise various pharmaceutically acceptable ingredients, such as antimicrobial preservatives and tonicity agents. Examples of suitable antimicrobial preservatives include: benzalkonium chloride, thimerosal, chlorobutanol, methyl paraben, propyl paraben, phenylethyl alcohol, edetate disodium, sorbic acid, Onamer M.™. and other agents equally well-known to those skilled in the art. Such preservatives, if utilized, will typically be employed in an amount between about 0.001 and about 1.0 wt %. Examples of suitable agents which may be used to adjust the tonicity or osmolality of the formulations include: sodium chloride, potassium chloride, mannitol, dextrose, glycerin, and propylene glycol. Such agents, if utilized, will typically be employed in an amount between about 0.1 and about 10.0 wt %. Determination of acceptable amounts of the above adjuvants is readily ascertained by one skilled in the art.

As will likewise be appreciated by those skilled in the art, the compositions may be formulated in various dosage forms suitable for topical ophthalmic delivery, as described above, including solutions, suspensions, emulsions, gels, and erodible solid ocular inserts. The compositions are preferably aqueous suspensions or solutions. Further, such formulated compositions may also include one or more additional active ingredients in a single vial for delivery to the patient. That is to say, in addition to one or more potassium channel inhibitors present in a single formulation, the present invention additionally contemplates the presence of one or more of the following therewith: miotics (e.g., pilocarpine, carbachol, and acetylcholinesterase inhibitors); sympathomimetics (e.g., epinephrine and dipivalylepinephrine); beta-blockers (e.g., betaxolol, levobunolol and timolol); alpha-2 agonists (e.g., para-amino clonidine); carbonic anhydrase inhibitors (e.g., acetazolamide, methazolamide and ethoxzolamide); and prostaglandins and their analogs and derivatives (e.g., latanaprost) in a single formulation for administration. One skilled in the art will recognize due care will need to be given in selecting such agents for co-administration from a single formulation with due regard for chemical stability and compatibility with other agents (whether active therapeutic agents or excipients) in the composition made available to the patient.

V. b) Effective Dosages

Pharmaceutical compositions suitable for use with the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to reduce sickle cell dehydration and/or delay the occurrence of erythrocyte sickling or distortion in situ, such compositions will contain an amount of active ingredient effective to achieve this result. Determination of an effective amount is well within the capabilities of those skilled in the art, especially in light of the detailed disclosure herein.

A therapeutically effective dose can also be determined from human data for compounds which are known to exhibit similar pharmacological activities, such as clotrimazole and other antimycotic agents (see, e.g., Brugnara et al., *JPET* 273:266-272 (1995)); Benzaquen et al., *Nature Medicine* 1: 534-540 (1995); Brugnara et al., *J. Clin. Invest.* 97(5): 1227-1234 (1996)). The applied dose can be adjusted based on the relative bioavailability and potency of the administered compound as compared with known glaucoma drugs.

Adjusting the dose to achieve maximal efficacy in humans based on the methods described above and other methods as are well-known in the art is well within the capabilities of the ordinarily skilled artisan.

In the case of local administration, the systemic circulating concentration of administered compound will not be of particular importance. In such instances, the compound is administered so as to achieve a concentration at the local area effective to achieve the intended result.

For use in the prophylaxis and/or treatment of sickle cell disease, including both chronic sickle cell episodes and acute sickle cell crisis, a circulating concentration of administered compound of about 0.001 µM to 20 µM is considered to be effective, with about 0.01 µM to 5 µM being preferred in some embodiments.

Patient doses for oral administration of the compounds described herein, which is the preferred mode of administration for prophylaxis and for treatment of chronic sickle cell episodes, typically range from about 1 mg/day to about 10,000 mg/day, more typically from about 10 mg/day to about 1,000 mg/day, and most typically from about 50 mg/day to about 500 mg/day. Stated in terms of patient body weight, typical dosages range from about 0.01 to about 150 mg/kg/day, more typically from about 0.1 to about 15 mg/kg/day, and most typically from about 1 to about 10 mg/kg/day.

For other modes of administration, dosage amount and interval can be adjusted individually to provide plasma levels of the administered compound effective for the particular clinical indication being treated. For example, if acute sickle crises are the most dominant clinical manifestation, in one embodiment, a compound according to the invention can be administered in relatively high concentrations multiple times per day. Alternatively, if the patient exhibits only periodic sickle cell crises on an infrequent, periodic or irregular basis, in one embodiment, it may be more desirable to administer a compound of the invention at minimal effective concentrations and to use a less frequent administration regimen. This will provide a therapeutic regimen that is commensurate with the severity of the individual's sickle cell disease.

Utilizing the teachings provided herein, an effective prophylactic or therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

V. Methods

In addition to the compounds and pharmaceutical formulations discussed in detail above, the present invention provides a number of methods in which the compounds of the invention find use. The methods range from those that might be used in a laboratory setting to probe the basic mechanisms of, for example, pharmacokinetics, drug activity, disease origin and progression and the like.

The compounds, compositions and methods of the present invention are further illustrated by the examples that follow. These examples are offered to illustrate, but not to limit the claimed invention.

EXAMPLES

General Materials and Methods

Reagents were used as received unless otherwise stated. All moisture-sensitive reactions were performed under a nitrogen atmosphere using oven dried glassware. Reactions were monitored by TLC on silica gel 60 $F_{254}$ with detection by charring with Hanessian's stain (Khadem et al., *Anal.*

*Chem.*, 1958, 30, (1965)). Column chromatography was carried out using silica gel (32-63 μM). Melting points were determined on an Electrothermal IA9000 unit and are uncorrected. $^1$H (300 MHz) and $^{19}$F (282 MHz) spectra were recorded on a Varian (Gemini 2000) NMR machine at room temperature in $CDCl_3$. Tetramethylsilane was used as the internal reference.

Example 1

Preparation of 3
 1.1 General Method
 To a solution of 6.6 mmol of 1 (1a or 1b) in 50 mL of anhydrous THF was added 33 mmol of 2 at room temperature under $N_2$. The reaction mixture was stirred for 0.5 h before quenched with saturated $NH_4Cl$. After the mixture was made basic with $NH_4OH$, the mixture was extracted with EtOAc. The organic phase was washed with saturated NaCl, dried over $MgSO_4$, and concentrated in vacuo. The residue was purified by column chromatography on silica gel to give 4.2 mmol of 3.
 1.2 Results
 Analytical data for exemplary compounds of the structure 3 are provided below.
  1.2.a (2-Chloro-6-methyl-pyridin-3-yl)-bis-(3-fluoro-phenyl)-methanol
   $^1$H NMR (300 MHz, $CDCl_3$) δ 7.35-7.26 (m, 2H), 7.05-6.91 (m, 8H), 2.54 (s, 3H); MS m/z: 346 (M+1).
  1.2.b Bis-(3-fluoro-phenyl)-(6-methyl-pyridin-3-yl)-methanol
   $^1$H NMR (300 MHz, $CDCl_3$) δ 8.27 (d, J=2.3 Hz, 1H), 7.51 (dd, J=8.2 Hz, $J_2$=2.4 Hz, 1H), 7.31-7.24 (m, 2H), 7.12 (d, J=8.0 Hz, 1H), 6.99-6.95 (m, 6H), 3.92 (bs, 1H), 2.55 (s, 3H); MS m/z: 312 (M+1).

Example 2

Preparation of 4
 2.1 General Method
 To 5.0 mmol of 3 in 50 mL of dichloromethane was added a 20% solution of acetyl chloride in dichloromethane (10 mL) at rt. The resulting solution was stirred for 12 h before the solvent was removed in vacuo to afford crude chloride intermediate which was used without purification in the next step.
 To the residue was added 5.5 mmol of copper cyanide and the resulting mixture was heated at 130° C. for 3 h. When the reaction mixture was cooled to 110° C., 30 mL of toluene was added and the mixture was stirred for 10 min. After mixture was filtered and the solvent was removed in vacuo, the residue was purified by column chromatography on silica gel to give 3.2 mmol of 4.
 2.2 Results
 Analytical data for exemplary compounds of the structure 4 are provided below.
  2.2.a (4-Fluoro-phenyl)-diphenyl-acetonitrile
   $^1$H NMR (300 MHz, $CDCl_3$) δ 7.48-7.28 (m, 6H), 7.27-7.17 (m, 6H), 7.04 (t, J=8.2 Hz, 2H), MS m/z: 288 (M+1).
  2.2.b Tris-(4-methoxy-phenyl)-acetonitrile
   $^1$H NMR (300 MHz, $CDCl_3$) δ 7.12 (d, J=8.9 Hz, 6H), 6.86 (d, J=8.8 Hz, 6H), 3.81 (s, 9H); MS m/z: 360 (M+1).
  2.2.c Bis-(4-methoxy-phenyl)-phenyl-acetonitrile
   $^1$H NMR (300 MHz, $CDCl_3$) δ 7.37-7.35 (m, 3H), 7.34-7.31 (m, 2H), 7.12 (d, J=8.9 Hz, 4H), 6.86 (d, J=8.8 Hz, 4H), 3.81 (s, 6H); MS m/z: 330 (M+1).

Example 3

Preparation of 6
 3.1 General Method
 A mixture of 14.5 mmol of 5, 2.9 mmol of acetonitrile, and 26.1 mmol of NaH (60% in mineral oil) in 30 mL of anhydrous toluene and 5 mL of 1,4-dioxane was stirred at 110° C. for one day. After being cooled to rt, the reaction mixture was quenched with saturated $NH_4Cl$, made basic with $NH_4OH$, and extracted with EtOAc. The organic phase was washed with saturated NaCl, dried over $MgSO_4$, and concentrated in vacuo. The residue was purified by column chromatography on silica gel to give 10.2 mmol of 6.
 3.2 Results
 Analytical data for an exemplary compound of the structure 6 are provided below.
  3.2.a Bis-(6-methyl-pyridin-2-yl)-acetonitrile
   $^1$H NMR (300 MHz, $CDCl_3$) δ 7.96-7.90 (m, 2H), 7.48 (dd, J=5.4 Hz, $J_2$=7.5 Hz, 2H), 6.93 (dd, J=8.3 Hz, $J_2$=2.8 Hz, 2H), 5.30 (s, 1H); MS m/z: 224 (M+1).

Example 4

Preparation of 7
 4.1 General Method
 A mixture of 5.2 mmol of 6 and 6.24 mmol of KH (30% in mineral oil) in excess of neat 5 or 30 mL of anhydrous toluene was stirred at 80° C. for 2 h. After cooled to room temperature, the reaction mixture was quenched with saturated $NH_4Cl$ and extracted with EtOAc. The organic phase was washed with saturated NaCl, dried over $MgSO_4$, and concentrated in vacuo. The residue was purified by column chromatography on silica gel to give 1.2 mmol of 7.
 4.2 Results
 Analytical data for an exemplary compound of the structure 7 are provided below.
  4.2.a Tris-(6-fluoro-pyridin-2-yl)-acetonitrile
   $^1$H NMR (300 MHz, $CDCl_3$) δ 7.85 (q, J=8.0 Hz, 3H), 7.38 (d, J=8.1 Hz, 3H), 6.94 (dd, J=8.2 Hz, $J_2$=3.0 Hz, 3H); MS m/z: 327 (M+1).

Example 5

Preparation of 8
 5.1 General Method
 A solution of concentrated sulfuric acid (10 mL) and glacial acetic acid (10 mL) was added to 5.0 mmol of 4 (or 7) at rt and the resulting solution was stirred at 130° C. for 3 h. The reaction mixture was cooled to 0° C. and neutralized by concentrated $NH_4OH$. After diluted with 30 mL of water, the mixture was extracted with chloroform (3×30 mL). The combined organic phase was washed with saturated NaCl, dried over $MgSO_4$, and concentrated in vacuo. The residue was purified by column chromatography on silica gel to give 2.2 mmol of 8.
 5.2 Results
 Analytical data for exemplary compounds of the structure 8 are provided below.
  5.2.a 2-(6-Fluoro-pyridin-2-yl)-2,2-diphenyl-acetamide
   $^1$H NMR (300 MHz, $CDCl_3$) δ 7.66 (q, J=8.0 Hz, 3H), 7.32-7.21 (m, 9H), 7.04-7.01 (m, 3H), 6.88 (dd, $J_1$=8.1 Hz, $J_2$=2.9 Hz, 1H), 6.75 (dd, $J_1$=7.8 Hz, $J_2$=2.2 Hz, 1H); MS m/z: 307 (M+1).
  5.2.b 2,2-Bis-(3-fluoro-phenyl)-2-(6-methyl-pyridin-3-yl)-acetamide $^1$H NMR (300 MHz, CDCl$_3$) δ 8.34 (d, J=2.3 Hz, 1H), 7.67 (dd, J$_1$=8.2 Hz, J$_2$=2.3 Hz, 1H), 7.31 (q, J=8.0 Hz, 2H), 7.18 (d, J=8.2 Hz, 1H), 7.06-6.93 (m, 6H), 2.6 (s, 3H); MS m/z: 339 (M+1).

5.2.c 2,2,2-Tris-(4-fluoro-phenyl)-acetamide $^1$H NMR (300 MHz, CDCl$_3$) δ 7.22 (dd, J$_1$=8.9 Hz, J$_2$=5.4 Hz, 8H), 7.01 (t, J=8.9 Hz, 6H), 5.77 (bs, 1H), 5.67 (bs, 1H); MS m/z: 342 (M+1).

Example 6

Preparation of 9

6.1 General Method

A mixture of 1.0 mmol of 8 and an excess of trimethyloxonium tetrafluoroborate in 20 mL of anhydrous dichloromethane was stirred overnight at rt before quenched with triethyl amine. The resulting mixture was diluted with 50 mL of dichloromethane, washed with saturated NaCl, dried over MgSO$_4$, and concentrated in vacuo. The residue was purified by column chromatography on silica gel to give 0.9 mmol of 9.

6.2 Results

Analytical data for an exemplary compound of the structure 9 is provided below.

6.2.a 2,2-Bis-(4-fluoro-phenyl)-2-phenyl-acetimidic acid methyl ester $^1$H NMR (300 MHz, CDCl$_3$) δ 7.32-7.30 (m, 3H), 7.13-7.09 (m, 6H), 6.99 (t, J=8.2 Hz, 4H), 3.83 (s, 3H); MS m/z: 338 (M+1).

Example 7

Preparation of 10

7.1 General Method

A mixture of 0.1 mmol of 9 and 5 mL of ammonia in methanol (0.5 mol) was stirred at 145° C. in a microwave reactor for 2 h. After the reaction mixture was cooled to rt, the solvent was removed in vacuo and the residue was purified by reverse phase HPLC to give 0.06 mmol of 10.

7.2 Results

Analytical data for an exemplary compound of the structure 10 is provided below.

7.2.a 2,2,2-Tris-(4-fluoro-phenyl)-acetamidine $^1$H NMR (300 MHz, CDCl$_3$) δ 7.24-7.19 (m, 6H), 7.05-6.97 (m, 6H), 5.88 (bs, 1H), 5.67 (bs, 1H); MS m/z: 341 (M+1).

Example 8

Preparation of 11

8.1 General Method

A mixture of 0.6 mmol of 9, 12 mmol of methoxylamine hydrochloride salt, and 1 mL of triethylamine in 5 mL of butanol was stirred overnight at 60° C. After the reaction mixture was cooled to room temperature, the solvents were removed. The mixture was dissolved in 100 mL of ethyl acetate and washed with saturated NaCl, dried over MgSO$_4$, and concentrated in vacuo. The residue was purified by column chromatography on silica gel to give 0.31 mmol of 11.

8.2 Results

Analytical data for exemplary compounds of the structure 11 are provided below.

8.2.a 2,2,2-Tris-(4-fluoro-phenyl)-N-hydroxy-acetamidine $^1$H NMR (300 MHz, CDCl$_3$) δ 7.25-7.19 (m, 2H), 7.17-7.13 (m, 3H), 7.10-7.03 (m, 3H), 6.97 (t, J=8.5 Hz, 6H); MS m/z: 357 (M+1).

8.2.b 2,2-Bis-(4-fluoro-phenyl)-N-methoxy-2-phenyl-acetamidine $^1$H NMR (300 MHz, CDCl$_3$) δ 7.30-7.22 (m, 9H), 6.95 (t, J=8.7 Hz, 4H), 3.80 (s, 3H); MS m/z: 353 (M+1).

8.2.c N-Hydroxy-2,2,2-triphenyl-acetamidine $^1$H NMR (300 MHz, CDCl$_3$) δ 7.38-7.34 (m, 9H), 7.29-7.21 (m, 9H); MS m/z: 303 (M+1).

Example 9

Preparation of 12

9.1 General Method

A mixture of 0.30 mmol of 9 and 1.5 mmol of hydrazine in 4 mL of butanol was stirred at 100° C. for 6 days. After the reaction mixture was cooled to rt, the solvent was removed in vacuo. The residue was purified by column chromatography on silica gel to give 0.14 mmol of 12.

9.2 Results

Analytical data for exemplary compounds of the structure 12 are provided below.

9.2.a 2,2-Bis-(4-fluoro-phenyl)-2-phenyl-acetamide-hydrazone $^1$H NMR (300 MHz, CDCl$_3$) δ 7.32-7.20 (m, 9H), 6.96 (t, J=8.7 Hz, 4H), 4.20 (bs, 2H); MS m/z: 338 (M+1).

9.2.b 2,2,2-Tris-(4-fluoro-phenyl)-2-phenyl-acetamide-hydrazone $^1$H NMR (300 MHz, CDCl$_3$) δ 7.38-7.36 (m, 2H), 7.26-7.16 (m, 8H), 7.05 (t, J=8.5 Hz, 6H); MS m/z: 356 (M+1).

Example 10

Preparation of 15

10.1 General Method

To a solution of 4.1 mmol of 14 in 25 mL of anhydrous THF at 0° C. was added 4.9 mmol of nBuLi (2.5 mol in hexane) under N$_2$, and the resulting mixture was stirred for 1 h and cooled to −78° C. To the cool solution was added 1.4 mmol of acetic anhydride and the mixture was stirred for 1 h before slowly warming to rt. The reaction was quenched with saturated NH$_4$Cl and extracted with EtOAc. The organic phase was washed with saturated NaCl, dried over MgSO$_4$, and concentrated in vacuo. The residue was purified by column chromatography on silica gel to give 1.2 mmol of 15.

10.2 Results

Analytical data for exemplary compound of the structure 15 is provided below.

10.2.a 1,1,1-Triphenyl-propan-2-one $^1$H NMR (300 MHz, CDCl$_3$) δ 7.33-7.21 (m, 15H), 2.10 (s, 3H); MS m/z: 287 (M+1).

Example 11

Preparation of 16

11.1 General Method

A solution of 0.17 mmol of 15 and excess substituted or unsubstituted amine, substituted or unsubstituted hydrazine in 10 mL of butanol was stirred at 100° C. for 4 days. After removal of the solvent, the residue was purified by column chromatography on silica gel to give 0.05 mmol of 16.

11.2 Results

Analytical data for exemplary compounds of the structure 16 are provided below.

11.2.a 1,1,1-Triphenyl-propan-2-one oxime
$^1$H NMR (300 MHz, CDCl$_3$) δ 7.35-7.19 (m, 15H), 1.93 (s, 3H); MS m/z: 302 (M+1).

11.2.b (1-Methyl-2,2,2-triphenyl-ethylidene)-hydrazine
$^1$H NMR (300 MHz, CDCl$_3$) δ 7.35-7.08 (m, 17H), 2.21 (s, 3H); MS m/z: 301 (M+1).

11.2.c 1,1,1-Triphenyl-propan-2-one O-methyl-oxime
$^1$H NMR (300 MHz, CDCl$_3$) δ 7.26-7.25 (m, 12H), 7.21-7.15 (m, 3H), 3.86 (s, 3H), 1.53 (s, 3H); MS m/z: 316 (M+1).

Example 12

Rubidium Efflux Assay

CHO-K1 cells (American Type Culture Collection, CCL-61) expressing human intermediate-conductance, calcium-activated K$^+$ channels (h-IK1) are cultured in Ham's F-12 medium (HyClone) supplemented with 10% heat inactivated fetal bovine serum (Nova-Tech) and 400 μg/mL G-418 (Geneticin, Life Technologies), in an incubator at 37° C. with a humidified atmosphere of 5% CO$_2$. Cells are typically subcultured twice per week. When the culture flask reaches 70%-90% confluency, the culture medium is removed, cells are rinsed twice with calcium and magnesium-free Dulbecco's phospate buffed saline (PBS) and a 0.05% trypsin/0.5 mM EDTA in HBSS solution is added until cells begin to round up (typically 2-5 min). Twenty four hours prior to the experiment, cells are removed from the culture flask and resuspended in Ham's F-12 medium supplemented with 10% heat inactivated fetal bovine serum, 50 μg/mL streptomycin, 50 U/mL penicillin, 10 mM HEPES, pH 7.2, and plated on 96 well, cell culture treated, flat bottomed trays (TPP 96, 4×10$^6$ cells per 96 well plate; 100 μL/well). Cells are loaded with $^{86}$Rb$^+$ by incubating the cells overnight in culture medium containing 1 μCi/ml $^{86}$RbCl (Perkin-Elmer) using a Labsystems Multidrop. On the day of the experiment, Culture media is removed and the cells are washed 4 times with 100 μL per well of zero Ca$^{2+}$ Earl's Balanced Salt Solution (EBSS)[composition (mM): NaCl (138), KCl (5.4), MgCl$_2$ (1), glucose (10), HEPES (10), pH 7.4 with 10N NaOH]. Cells were preincubated with drug (0.01-30 μM) in low Ca$^{2+}$ EBSS, [composition (mM): NaCl (138), CaCl$_2$ (0.25), KCl (5.4), MgCl$_2$ (1), glucose (10), HEPES (10), pH 7.4 with 10N NaOH] for 6 min. $^{86}$Rb$^+$ efflux is stimulated by exposing cells to regular EBSS [composition (mM): NaCl (138), CaCl$_2$ (1.8), KCl (5.4), MgCl$_2$ (1), glucose (10), HEPES (10), pH 7.4 with 10N NaOH] supplemented with 3 M ionomycin (Calbiochem), in the continued presence of drug. After a 10 min efflux period, the EBSS/ionomycin solution is removed from the cells and the $^{86}$Rb$^+$ content determined by Cherenkov counting (Wallac 1450 Microbeta Trilux liquid scintillation and luminescence counter). Cells are then lysed with 100 μL 0.1% SDS solution per well, and the $^{86}$Rb$^+$ content of the lysate determined. Percent $^{86}$Rb$^+$ efflux is calculated according to the following formula: ($^{86}$Rb$^+$ content in EBSS/($^{86}$Rb$^+$ content in EBSS+$^{86}$Rb$^+$ content of the lysate))×100.

TABLE 1 hIK1 Inhibitory Activity

| Example | Compound | IK1 Inhibitory Activity |
|---|---|---|
| 1 | 2-(2-Fluoro-phenyl)-2-(4-fluoro-phenyl)-N-hydroxy-2-phenyl-acetamidine | ++++ |
| 2 | 2,2-Bis-(4-fluoro-phenyl)-N-hydroxy-2-phenyl-acetamidine | ++++ |
| 3 | 2,2,2-Tris-(4-fluoro-phenyl)-N-hydroxy-acetamidine | ++++ |
| 4 | N-Ethoxy-2,2,2-tris-(4-fluoro-phenyl)-acetamidine | ++++ |
| 5 | 2-(2-Chloro-phenyl)-2,2-bis-(4-fluoro-phenyl)-N-hydroxy-acetamidine | ++++ |
|   | 2-(2-Chloro-phenyl)-N-hydroxy-2,2-diphenyl-acetamidine | ++++ |
| 6 | (2-Chloro-phenyl)-diphenyl-acetaldehyde oxime | ++++ |
| 7 | (2-Chloro-phenyl)-diphenyl-acetaldehyde O-methyl-oxime | ++++ |
| 8 | 2,2-Bis-(4-fluoro-phenyl)-N-methoxy-2-phenyl-acetamidine | ++++ |
| 9 | 2,2-Bis-(4-fluoro-phenyl)-N-amino-2-phenyl-acetamidine | +++ |
| 10 | 2,2,2-Tris-(4-fluoro-phenyl)-N-amino-acetamidine | +++ |
| 11 | N-Hydroxy-2,2,2-triphenyl-acetamidine | +++ |
| 12 | N-Hydroxy-2-(4-methoxy-phenyl)-2,2-diphenyl-acetamidine | +++ |
| 13 | 2-(6-Fluoro-pyridin-2-yl)-N-hydroxy-2,2-diphenyl-acetamidine | +++ |
| 14 | 2-(3-Fluoro-phenyl)-2,2-bis-(6-fluoro-pyridin-2-yl)-N-hydroxy-acetamidine | ++ |
| 15 | 2,2,2-Tris-(6-fluoro-pyridin-2-yl)-acetamidine | ++ |
| 16 | 2-Fluoro-6-[(5-methyl-[1,2,4]oxadiazol-3-yl)-diphenyl-methyl]-pyridine | ++ |
| 17 | 2,2-Bis-(3-fluoro-phenyl)-2-(6-methyl-pyridin-3-yl)-acetamidine | ++ |
| 18 | 2,2,2-Tris-(4-fluoro-phenyl)-acetamidine | ++ |
| 19 | 2,2,2-Tris-(4-fluoro-phenyl)-N-methoxy-acetamidine | ++ |
| 20 | 2,2,2-Tris-(4-fluoro-phenyl)-N-isopropoxy-acetamidine | ++ |
| 21 | 2,2-Bis-(4-fluoro-phenyl)-2-phenyl-acetamidine | ++ |
| 22 | 2,2,2-Triphenyl-acetamidine | ++ |
| 23 | N-Hydroxy-2,2-bis-(4-methoxy-phenyl)-2-phenyl-acetamidine | ++ |

TABLE 1-continued hIK1 Inhibitory Activity

| Example | Compound | IK1 Inhibitory Activity |
|---|---|---|
| 24 | N-Hydroxy-2-(4-hydroxy-phenyl)-2,2-diphenyl-acetamidine | ++ |
| 25 | (1-Methyl-2,2,2-triphenyl-ethylidene)-hydrazine | ++ |
| 26 | 1,1,1-Triphenyl-propan-2-one O-methyl-oxime | ++ |
| 27 | 2,2,2-Tris-(4-fluoro-phenyl)-acetimidic acid methyl ester | ++ |
| 28 | 2,2-Bis-(4-fluoro-phenyl)-2-phenyl-acetimidic acid methyl ester | ++ |
| 29 | 2,2-Bis-(4-fluoro-phenyl)-N-methyl-2-phenyl-acetimidic acid methyl ester | ++ |
| 30 | 2,2,2-Tris-(6-fluoro-pyridin-2-yl)-N-hydroxy-acetamidine | + |
| 31 | N-Hydroxy-2,2,2-tris-(4-methoxy-phenyl)-acetamidine | + |
| 32 | N-Hydroxy-2,2-bis-(4-hydroxy-phenyl)-2-phenyl-acetamidine | + |
| 33 | 1,1,1-Triphenyl-propan-2-one O-ethyl-oxime | + |
| 34 | 1,1,1-Triphenyl-propan-2-one oxime | + |

Key:
+ indicates IC50 > 10 μM;
++ indicates 10 μM > IC50 > 1.0 μM;
+++ indicates 1.0 μM > IC50 > 0.5 μM;
++++ indicates IC50 < 0.5 μM.

Example 13

Utilizing the methods set forth herein, the following compounds were prepared.

TABLE 2

Examples

| Example | Compounds |
|---|---|
| 1 | 2-(2-Fluoro-phenyl)-2-(4-fluoro-phenyl)-N-hydroxy-2-phenyl-acetamidine |
| 2 | 2-(6-Fluoro-pyridin-2-yl)-N-hydroxy-2,2-diphenyl-acetamidine |
| 3 | 2-(3-Fluoro-phenyl)-2,2-bis-(6-fluoro-pyridin-2-yl)-N-hydroxy-acetamidine |
| 4 | 2,2,2-Tris-(6-fluoro-pyridin-2-yl)-acetamidine |
| 5 | 2-Fluoro-6-[(5-methyl-[1,2,4]oxadiazol-3-yl)-diphenyl-methyl]-pyridine |
| 6 | 2,2-Bis-(3-fluoro-phenyl)-2-(6-methyl-pyridin-3-yl)-acetamidine |
| 7 | 2,2-Bis-(3-fluoro-phenyl)-2-(6-methyl-pyridin-3-yl)-acetamidine |
| 8 | 2,2-Bis-(4-fluoro-phenyl)-N-amino-2-phenyl-acetamidine |
| 9 | 2,2,2-Tris-(4-fluoro-phenyl)-N-hydroxy-acetamidine |
| 10 | 2,2,2-Tris-(4-fluoro-phenyl)-N-amino-acetamidine |
| 11 | 2,2,2-Tris-(4-fluoro-phenyl)-acetamidine |
| 12 | 2,2,2-Tris-(4-fluoro-phenyl)-N-methoxy-acetamidine |
| 13 | N-Ethoxy-2,2,2-tris-(4-fluoro-phenyl)-acetamidine |
| 14 | 2,2,2-Tris-(4-fluoro-phenyl)-N-isopropoxy-acetamidine |
| 15 | N-Hydroxy-2,2,2-triphenyl-acetamidine |
| 16 | 2,2-Bis-(4-fluoro-phenyl)-2-phenyl-acetamidine |
| 17 | 2,2,2-Triphenyl-acetamidine |
| 18 | N-Hydroxy-2,2-bis-(4-methoxy-phenyl)-2-phenyl-acetamidine |
| 19 | N-Hydroxy-2,2,2-tris-(4-methoxy-phenyl)-acetamidine |
| 20 | N-Hydroxy-2,2-bis-(4-hydroxy-phenyl)-2-phenyl-acetamidine |
| 21 | 2-(2-Chloro-phenyl)-2,2-bis-(4-fluoro-phenyl)-N-hydroxy-acetamidine |
| 22 | 2-(2-Chloro-phenyl)-N-hydroxy-2,2-diphenyl-acetamidine |
| 23 | 2,2-Bis-(4-fluoro-phenyl)-N-methoxy-2-phenyl-acetamidine |
| 24 | N-Hydroxy-2-(4-methoxy-phenyl)-2,2-diphenyl-acetamidine |
| 25 | N-Hydroxy-2-(4-hydroxy-phenyl)-2,2-diphenyl-acetamidine |
| 26 | 3,3-Diphenyl-indan-1,2-dione 2-(O-methyl-oxime) |
| 27 | 1,1,1-Triphenyl-propan-2-one oxime |

TABLE 2-continued

Examples

| Example | Compounds |
|---|---|
| 28 | (1-Methyl-2,2,2-triphenyl-ethylidene)-hydrazine |
| 29 | 1,1,1-Triphenyl-propan-2-one O-methyl-oxime |
| 30 | 1,1,1-Triphenyl-propan-2-one O-ethyl-oxime |
| 31 | (2-Chloro-phenyl)-diphenyl-acetaldehyde oxime |
| 32 | (2-Chloro-phenyl)-diphenyl-acetaldehyde O-methyl-oxime |
| 33 | 2,2,2-Tris-(4-fluoro-phenyl)-acetimidic acid methyl ester |
| 34 | 2,2-Bis-(4-fluoro-phenyl)-2-phenyl-acetimidic acid methyl ester |
| 35 | 2,2-Bis-(4-fluoro-phenyl)-N-methyl-2-phenyl-acetimidic acid methyl ester |
| 36 | 2,2,2-Tris-(6-fluoro-pyridin-2-yl)-N-hydroxy-acetamidine |
| 37 | 1-(2-Chloro-phenyl)-1,1-bis-(4-fluoro-phenyl)-propan-2-one O-(2-aminoacetyl)-oxime |
| 38 | N'-[2-(2-Chloro-phenyl)-2,2-bis-(4-fluoro-phenyl)-1-methyl-ethylidene]-phosphorohydrazidic acid |
| 39 | Amino-acetic acid [2-(2-chloro-phenyl)-2,2-bis-(4-fluoro-phenyl)-1-methyl-ethylidene]-hydrazide |
| 40 | Acetic acid [1-amino-2-(2-chloro-phenyl)-2,2-bis-(4-fluoro-phenyl)-ethylidene]-hydrazide |
| 41 | Amino-acetic acid [1-amino-2-(2-chloro-phenyl)-2,2-bis-(4-fluoro-phenyl)-ethylidene]-hydrazide |
| 42 | N-[1-Amino-2-(2-chloro-phenyl)-2,2-bis-(4-fluoro-phenyl)-ethylidene]-methanesulfonamide |
| 43 | 2-(2-Chloro-phenyl)-2,2-bis-(4-fluoro-phenyl)-N-nitrile-acetamidine |
| 44 | N-[2-(2-Chloro-phenyl)-2,2-bis-(4-fluoro-phenyl)-1-imino-ethyl]-guanidine |
| 45 | N-[2-(2-Chloro-phenyl)-2,2-bis-(4-fluoro-phenyl)-1-methoxyimino-ethyl]-guanidine |
| 46 | N-Acetyl-N'-[2-(2-chloro-phenyl)-2,2-bis-(4-fluoro-phenyl)-1-imino-ethyl]-guanidine |
| 47 | Phosphoric acid mono-[4-(carbamimidoyl-diphenyl-methyl)-phenyl] ester |
| 48 | Na salt of phosphoric acid mono-[4-(carbamimidoyl-diphenyl-methyl)-phenyl] ester |
| 49 | Phosphoric acid 4-(carbamimidoyl-diphenyl-methyl)-phenyl ester dimethyl ester |
| 50 | Amino-acetic acid 4-(carbamimidoyl-diphenyl-methyl)-phenyl ester |
| 51 | 2-Amino-propionic acid 4-(carbamimidoyl-diphenyl-methyl)-phenyl ester |
| 52 | Phosphoric acid mono-{4-[(N-hydroxycarbamimidoyl)-diphenyl-methyl]-phenyl} ester |
| 53 | Amino-acetic acid 4-[(N-hydroxycarbamimidoyl)-diphenyl-methyl]-phenyl ester |
| 54 | Phosphoric acid mono-[4-(2-aminoimino-1,1-diphenyl-propyl)-phenyl] ester |
| 55 | Amino-acetic acid 4-[(N-aminocarbamimidoyl)-diphenyl-methyl]-phenyl ester |
| 56 | Phosphoric acid mono-[4-(2-hydroxyimino-1,1-diphenyl-propyl)-phenyl] ester |
| 57 | Amino-acetic acid 4-(2-hydroxyimino-1,1-diphenyl-propyl)-phenyl ester |
| 58 | Phosphoric acid mono-[4-(2-hydroxyimino-1,1-diphenyl-propyl)-phenyl] ester |
| 59 | Amino-acetic acid 4-(2-hydrazono-1,1-diphenyl-propyl)-phenyl ester |
| 60 | Phosphoric acid mono-[4-(2-hydroxyimino-1,1-diphenyl-ethyl)-phenyl] ester |
| 61 | Amino-acetic acid 4-(2-hydroxyimino-1,1-diphenyl-ethyl)-phenyl ester |
| 62 | Phosphoric acid mono-[4-(2-guanidino-2-imino-1,1-diphenyl-ethyl)-phenyl] ester |
| 63 | Amino-acetic acid 4-(2-guanidino-2-imino-1,1-diphenyl-ethyl)-phenyl ester |

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A compound having a structure according to Formula (I):

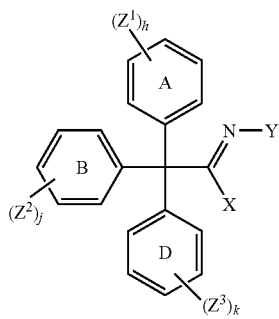

or pharmaceutically acceptable salts thereof, wherein
X is H, substituted or unsubstituted alkyl or —NR$^2$R$^3$,
Y is H or —OR$^7$;
Z$^1$, Z$^2$, and Z$^3$ are independently H, hydroxyl, amino, cyano, nitro, halogen, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, —SR$^{4b}$, —OR$^{5b}$, —P(O)R$^{10a}$R$^{11a}$, —S(O)$_{q1}$R$^{12a}$, or —PR$^{14}$R$^{15}$, wherein q1 is an integer selected from 1 and 2;
h, j, and k are integers independently selected from 1 to 5;
R$^2$ is H, hydroxyl, amino, substituted or unsubstituted alkyl, substituted or unsubstituted cycloalkyl, substituted or unsubstituted heteroalkyl, or substituted or unsubstituted heterocycloalkyl;
R$^3$ is H, hydroxyl, amino, substituted or unsubstituted alkyl, substituted or unsubstituted cycloalkyl, substituted or unsubstituted heteroalkyl, substituted or unsubstituted heterocycloalkyl, —P(O)R$^{10c}$R$^{11c}$, —S(O)$_{q3}$Rl$^{12C}$, or —C(O)R$^{17b}$,
wherein q3 is an integer selected from 1 and 2, and
wherein R$^2$ and R$^3$ are optionally joined to form a substituted or unsubstituted heterocycloalkyl or substituted or unsubstituted heteroaryl with the nitrogen to which they are attached;
R$^{4b}$ is H, substituted or unsubstituted alkyl, substituted or unsubstituted cycloalkyl, substituted or unsubstituted heteroalkyl, or substituted or unsubstituted heterocycloalkyl;
R$^{5b}$ is H, substituted or unsubstituted alkyl, substituted or unsubstituted cycloalkyl, substituted or unsubstituted heteroalkyl, substituted or unsubstituted heterocycloalkyl, —P(O)R$^{10d}$R$^{11d}$, or —S(O)$_{q4}$R$^{12d}$, wherein q4 is an integer selected from 1 and 2;
R$^7$ is H, substituted or unsubstituted alkyl, substituted or unsubstituted cycloalkyl, substituted or unsubstituted heteroalkyl, substituted or unsubstituted heterocycloalkyl, or —P(O)R$^{10f}$R$^{11f}$ and;
R$^{10a}$, R$^{10c}$, R$^{10d}$, R$^{10f}$, R$^{11a}$, R$^{11c}$, R$^{11d}$ and R$^{11f}$ are independently amino, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, or —OR$^{16}$, wherein R$^{16}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl,
wherein R$^{10a}$ and R$^{11a}$, R$^{10c}$ and R$^{11c}$, R$^{10d}$ and R$^{11d}$, R$^{10f}$ and R$^{11f}$ are not simultaneously amino;
R$^{12a}$, R$^{12c}$ or R$^{12d}$ is independently amino, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl;
R$^{14}$ and R$^{15}$ are independently substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl; and
R$^{17b}$ is H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or —OR$^8$, wherein
R$^{18}$ is H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl
wherein Y and X, together with the atoms to which they are attached, are optionally joined to form a substituted or unsubstituted ring;
wherein Z$^1$ and X, together with the atoms to which they are attached, are optionally joined to form a bicyclic fused ring;
wherein Z$^3$ and X, together with the atoms to which they are attached, are optionally joined to form a bicyclic fused ring;
wherein Z$^1$ and Z$^2$, together with the atoms to which they are attached, are optionally joined to form a tricyclic fused ring;
wherein Z$^1$ and Z$^3$, together with the atoms to which they are attached, are optionally joined to form a tricyclic fused ring; and
wherein Z$^2$ and Z$^3$, together with the atoms to which they are attached, are optionally joined to form a tricyclic fused ring;
wherein at least two of the ring hydrogen atoms among A, B and D rings are substituted.

2. The compound of claim 1, wherein X is hydrogen, —NH$_2$, —N(H)C(NH)NH$_2$, or substituted or unsubstituted C$_1$-C$_{10}$ alkyl.

3. The compound of claim 1, wherein Z$^1$, Z$^2$, and Z$^3$ are independently H, hydroxyl, halogen, substituted or unsubstituted alkyl, substituted or unsubstituted heteroalkyl, —P(O)R$^{10a}$R$^{11a}$, or —S(O)R$^{12a}$.

4. The compound of claim 1, wherein
X is H or unsubstituted alkyl;
R$^7$ is H, unsubstituted alkyl, unsubstituted cycloalkyl, unsubstituted heteroalkyl, or unsubstituted heterocycloalkyl; and
Z$^1$, Z$^2$, and Z$^3$ are independently H, hydroxyl, amino, cyano, nitro, or halogen, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl.

5. The compound of claim 4, wherein Z$^1$, Z$^2$, and Z$^3$ are independently H or halogen.

6. The compound of claim 5, wherein the halogen is fluorine.

7. The compound of claim 6, wherein the compound has a structure according to the formula:

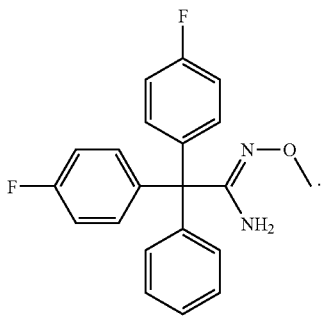

8. A pharmaceutical composition comprising the compound of claim 1 in admixture with a pharmaceutically acceptable excipient.

9. The composition of claim 8, wherein
X is H or unsubstituted alkyl;
$R^7$ is H, unsubstituted alkyl, unsubstituted cycloalkyl, unsubstituted heteroalkyl, or unsubstituted heterocycloalkyl; and
$Z^1$, $Z^2$, and $Z^3$ are independently H, hydroxyl, amino, cyano, nitro, or halogen, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl.

10. The composition of claim 9, wherein $Z^1$, $Z^2$, and $Z^3$ are independently H or halogen.

11. The composition of claim 10, wherein the halogen is fluorine.

12. The composition of claim 11, wherein the compound has a structure according to the formula:

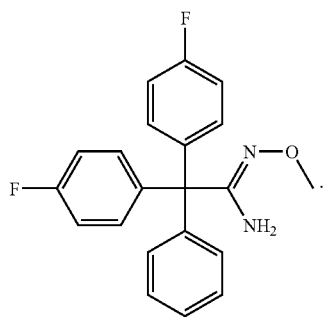

13. A method for treating a sickle cell disease event, said method comprising administering to a subject suffering sickle cell disease a therapeutically effective amount of composition of claim 8.

* * * * *

UNITED STATES PATENT AND TRADEMARK OFFICE
CERTIFICATE OF CORRECTION

| | | |
|---|---|---|
| PATENT NO. | : 7,709,533 B2 | |
| APPLICATION NO. | : 11/346546 | |
| DATED | : May 4, 2010 | |
| INVENTOR(S) | : Wang et al. | |

It is certified that error appears in the above-identified patent and that said Letters Patent is hereby corrected as shown below:

Title Page:

In the face sheet, second column, at References Cited Section (56) (OTHER PUBLICATIONS): please delete "Brugnara, C. et al., "Therapy with Oral Clotimazole Induces Inhibition of the Gardos Channel and Reduction of Erythrocyte Dehydration in Patients with Sickle Cell Disease," J. Clin. Invest., 1996, vol. 97 No. 5, pp. 1227-1234" and insert --Brugnara, C. et al., "Therapy with Oral Clotrimazole Induces Inhibition of the Gardos Channel and Reduction of Erythrocyte Dehydration in Patients with Sickle Cell Disease," J. Clin. Invest., 1996, vol. 97, No. 5, pp. 1227-1234--.

In the face sheet, second column, at References Cited Section (56) (OTHER PUBLICATIONS): please delete "De Franceschi, L. et al., "Treatment with Oral Clotrimazole blocks $Ca^{2+}$-activated $K^+$ transport and reverses Erythrocyte Dehydration in Transgenic SAD mice; *A model for therapy of sickel cell disease*," J. Clin, invest., 1994, vol. 93, pp. 1670-1676" and insert --De Franceschi, L. et al., "Treatment with Oral Clotrimazole blocks $Ca^{2+}$-activated $K^+$ transport and reverses Erythrocyte Dehydration in Transgenic SAD mice; *A model for therapy of sickle cell disease*," J. Clin. Invest., 1994, vol. 93, pp. 1670-1676--.

In the face sheet, second column, at References Cited Section (56) (OTHER PUBLICATIONS): please delete "Zhang, JJ et al., "Three different Cl channels in the bovine ciliary epithelium activated by hypotonic stress," J. Physiol., 1997, vol. 499 Issue 2, pp. 379-389" and insert --Zhang, JJ et al., "Three different Cl⁻ channels in the bovine ciliary epithelium activated by hypotonic stress," J. Physiol., 1997, vol. 499, Issue 2, pp. 379-389--.

In the Claims:

Claim 1, Column 55, Line 22: at the end of the line, please delete "," (delete the second comma), and insert --;-- (i.e., replace second comma with a semicolon, at the end of the line).

Signed and Sealed this
Eighteenth Day of January, 2011

David J. Kappos
*Director of the United States Patent and Trademark Office*

CERTIFICATE OF CORRECTION (continued)
U.S. Pat. No. 7,709,533 B2

Claim 1, Column 55, Line 33: please insert a space between "$R^2$" and "is".

Claim 1, Column 55, Line 41: please delete "$RI^{12c}$" and insert --$R^{12c}$--.

Claim 1, Column 56, Line 22: please delete "—$OR^8$" please insert -- —$OR^{18}$--.

Claim 1, Column 56, Line 23: after "is" please insert --independently--.